(12) United States Patent
Deliwala et al.

(10) Patent No.: US 9,733,275 B2
(45) Date of Patent: Aug. 15, 2017

(54) CIRCUIT ARCHITECTURE FOR MODE SWITCH

(71) Applicant: ANALOG DEVICES, INC., Norwood, MA (US)

(72) Inventors: Shrenik Deliwala, Andover, MA (US); Steven J. Decker, Sandown, NH (US); Gregory T. Koker, Newton, MA (US); Dan M. Weinberg, Westford, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 0 days.

(21) Appl. No.: 14/808,148

(22) Filed: Jul. 24, 2015

(65) Prior Publication Data

US 2016/0025777 A1  Jan. 28, 2016

Related U.S. Application Data

(60) Provisional application No. 62/029,361, filed on Jul. 25, 2014.

(51) Int. Cl.
*G01R 1/38* (2006.01)
*G01R 15/09* (2006.01)
(Continued)

(52) U.S. Cl.
CPC .......... *G01R 15/09* (2013.01); *A61B 5/02427* (2013.01); *G01J 1/44* (2013.01);
(Continued)

(58) Field of Classification Search
CPC ........ G01R 19/25; G01R 15/08; G01N 33/53; G01N 27/305; G01N 25/56; H01L 2224/48091; H01L 2924/181
(Continued)

(56) References Cited

U.S. PATENT DOCUMENTS 7,960,679 B2  6/2011  Fann
7,978,311 B2  7/2011  Deliwala
(Continued)

FOREIGN PATENT DOCUMENTS

DE  10-2014-105398  10/2014
KR  11-506544  6/1999
(Continued)

OTHER PUBLICATIONS

International Search Report and Written Opinion issued in PCT Patent Application Serial No. US/2015/042148 mailed Dec. 3, 2015, 8 pages.
(Continued)

*Primary Examiner* — Melissa Koval
*Assistant Examiner* — Trung Nguyen
(74) *Attorney, Agent, or Firm* — Patent Capital Group

(57) ABSTRACT

A current detection module capable of differentiating and quantifying contribution to a current signal generated by a sensor in response to stimulation by a certain target source from contributions from sources other than the target source (ambient sources) is disclosed. As long as the contribution from the target source comprises a pulsed signal, the module may synchronize itself to the pulse(s) so that there is a predetermined phase relationship between the pulse(s) and functions carried out by various stages of the module. The module may be re-used to also detect and quantify contributions from ambient sources by presenting these contributions to the module as pulses that trigger synchronization of the module. To that end, a detection system disclosed herein is based on the use of such current detection module and allows mode switching where, depending on the selected mode of operation, the module is configured to perform different measurements.

27 Claims, 15 Drawing Sheets

(51) Int. Cl.
G01J 1/44 (2006.01)
G01R 19/25 (2006.01)
A61B 5/024 (2006.01)
G01R 15/08 (2006.01)

(52) U.S. Cl.
CPC ........ *G01R 19/25* (2013.01); *G01J 2001/446* (2013.01); *G01R 15/08* (2013.01)

(58) Field of Classification Search
USPC .. 324/600, 713, 500–521, 522, 764.01, 718, 324/115, 76.11, 234, 239, 200, 607, 120; 257/431, E31.124; 702/60–65, 297, 298
See application file for complete search history.

(56) References Cited

U.S. PATENT DOCUMENTS

| | | | |
|---|---|---|---|
| 9,130,070 | B2 | 9/2015 | Deliwala |
| 2005/0258885 | A1 | 11/2005 | Ono |
| 2007/0080905 | A1 | 4/2007 | Takahara |
| 2009/0127461 | A1 | 5/2009 | Holcombe et al. |
| 2011/0114842 | A1 | 5/2011 | Ji et al. |
| 2014/0285472 | A1* | 9/2014 | Raynor ................. G06F 3/0416 345/175 |
| 2014/0323844 | A1 | 10/2014 | Deliwala et al. |
| 2014/0323874 | A1* | 10/2014 | Addison ............ A61B 5/14552 600/473 |
| 2015/0333712 | A1 | 11/2015 | Deliwala et al. |

FOREIGN PATENT DOCUMENTS

| | | |
|---|---|---|
| KR | 10-1701560 | 2/2017 |
| WO | 98/18205 | 4/1998 |

OTHER PUBLICATIONS

1st Action Notice of Allowance issued in U.S. Appl. No. 13/860,669 dated Apr. 28, 2015, 11 pages.
OA1 issued in KR Patent Application Serial No. 10-2014-48009 dated Feb. 25, 2016, 7 pages.
English Summary of OA1 issued in KR Patent Application Serial No. 10-2014-48009 dated Feb. 25, 2016, 5 pages.
Models 1601 and 1611 User's Manual, "High-Speed Photoreceivers", 12 pages.
G. Lochead, "Photodiode Amplifiers", 8 pages.
Chirag J. Pujary, "Investigation of Photodetector Optimization in Reducing Power Consumption by a Noninvasive Pulse Oximeter Sensor", Jan. 16, 2004, 133 pages.
Humaira Taz, "Radon Detection Using A PIN Photodiode", Wesleyan College, 16 pages.
Patrick J. Windpassinger et al., "Ultra Low-Noise Differential Ac-Coupled Photodetector For Sensitive Pulse Detection Applications", Measurement Science and Technology 20 (2009) 0957-0233/09/055301, 2009 IOP Publishing Ltd., 7 pages.
"Integrated Photodiode and Amplifier", Burr-Brown, OPT201, 1993 Burr-Brown Corporation, PDS-1180B, Jan. 1995, 11 pages.
"Photodiode Typical Operating Circuits", AP Technologies, www.aptechnologies.co.uk, 2 pages.
David Westerman, "Understand and Apply The Transimpedance Amplifier" (Part 1 of 2), Planet Analog, Aug. 8, 2007, 8 pages.
"Designing Photodiode Amplifier Circuits With OPA128", Burr-Brown, AB077, 1994 Burr-Brown Corporation, Jan. 1994, 4 pages.
"SHM-180—Eight Channel Sample & Hold Module", Becker & Hickl GmbH, Apr. 2003, 13 pages.
"Application Circuit Examples of Si Photodiode", Hamamatsu Photonics K.K., Solid State Division, Jun. 2004, 4 pages.
English Translation of Letters Patent for KR10-2014-0048009 dated Feb. 1, 2017.

* cited by examiner

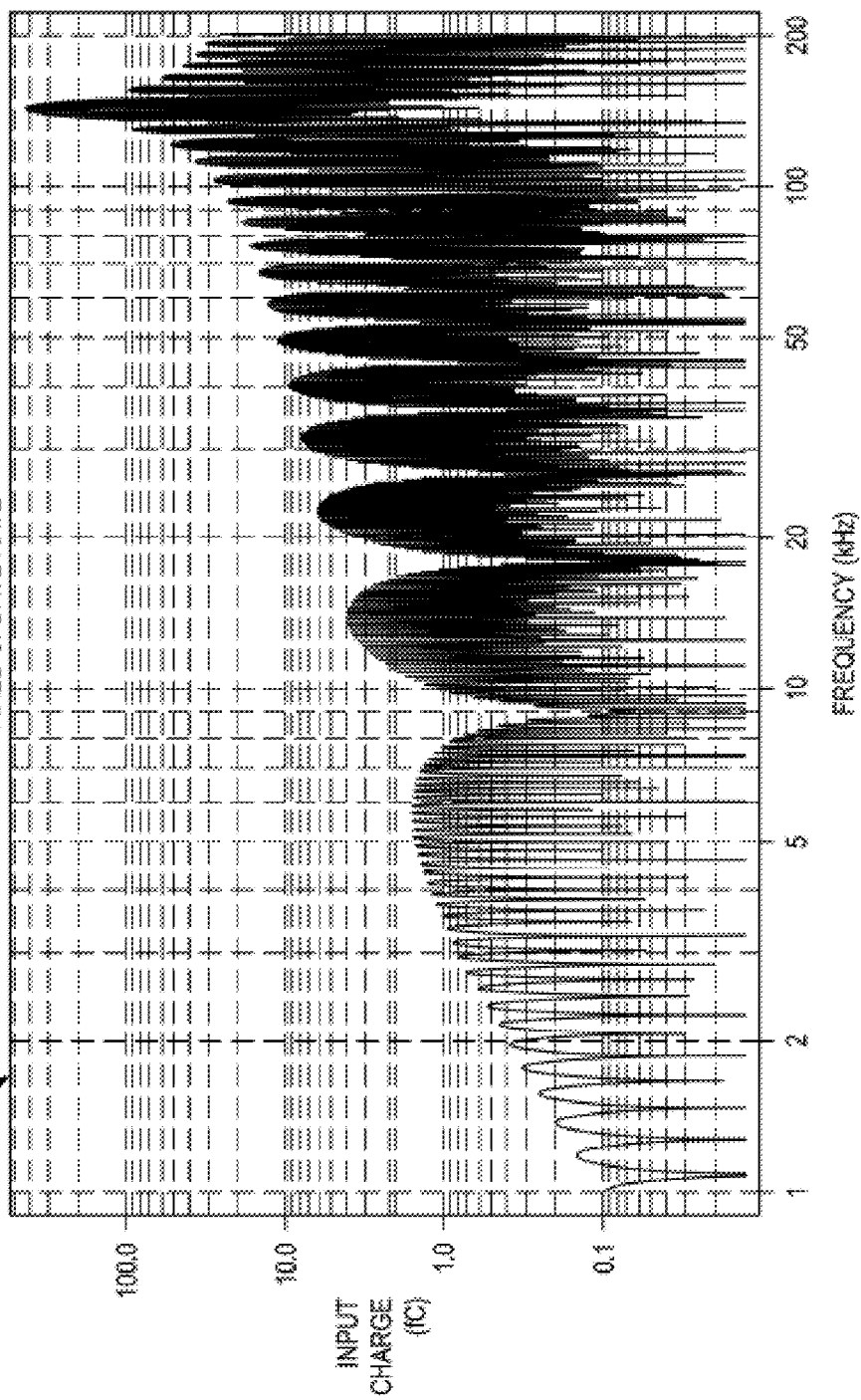

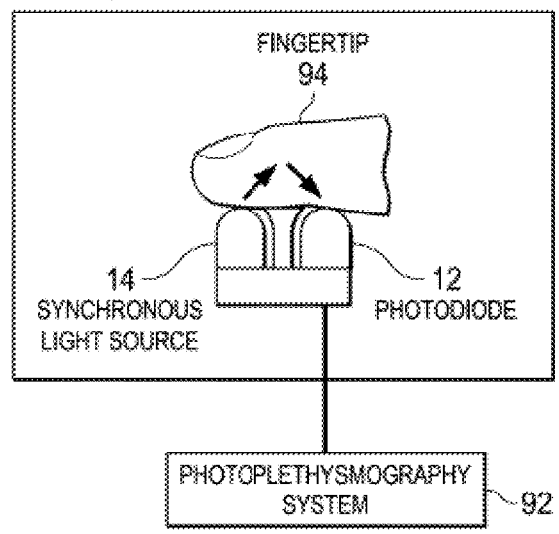
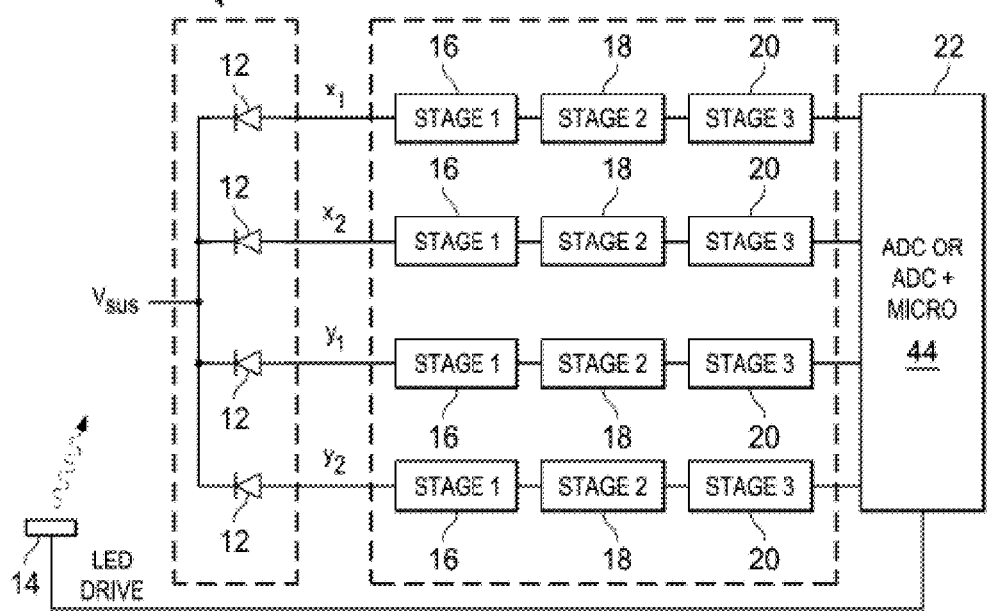

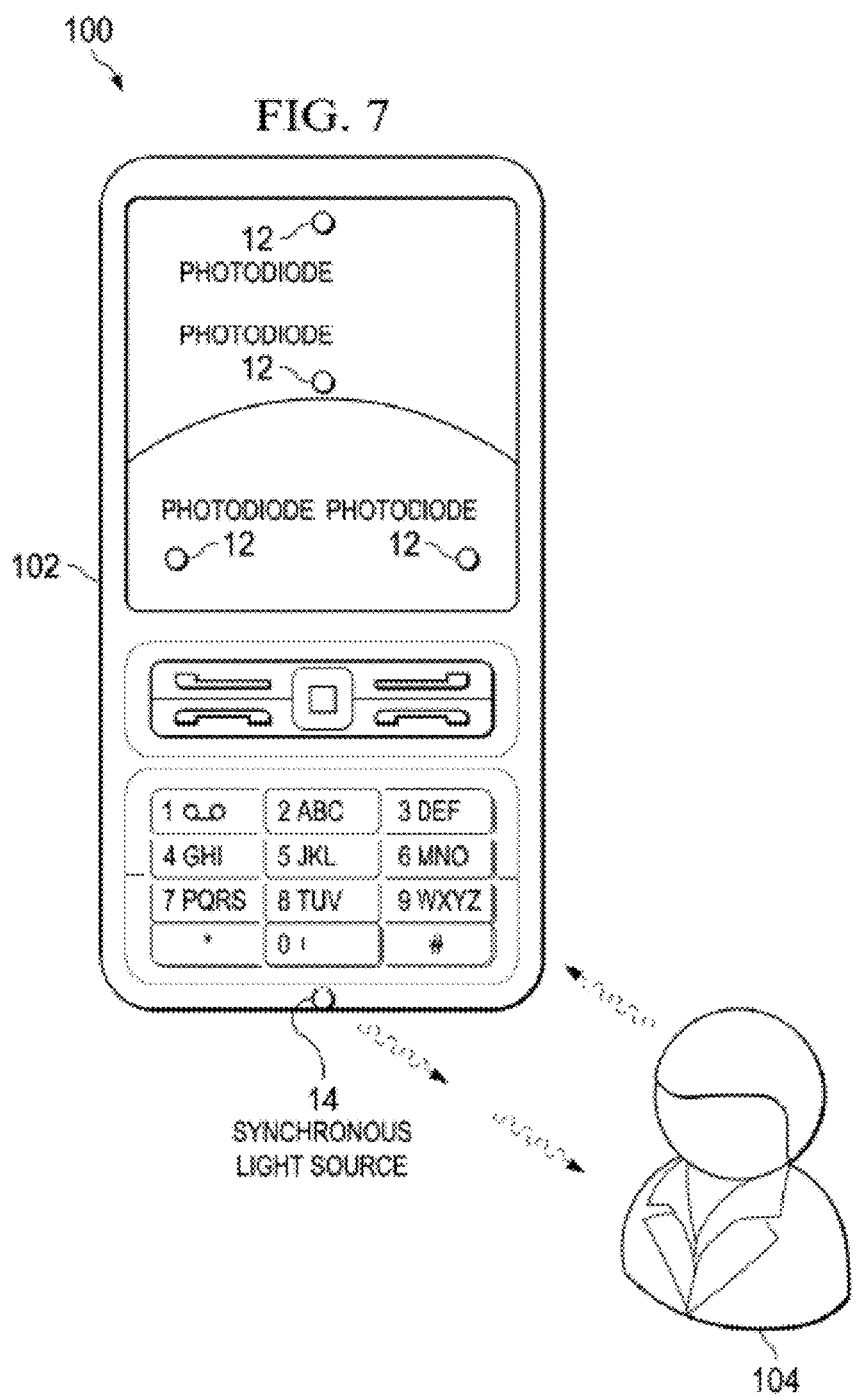

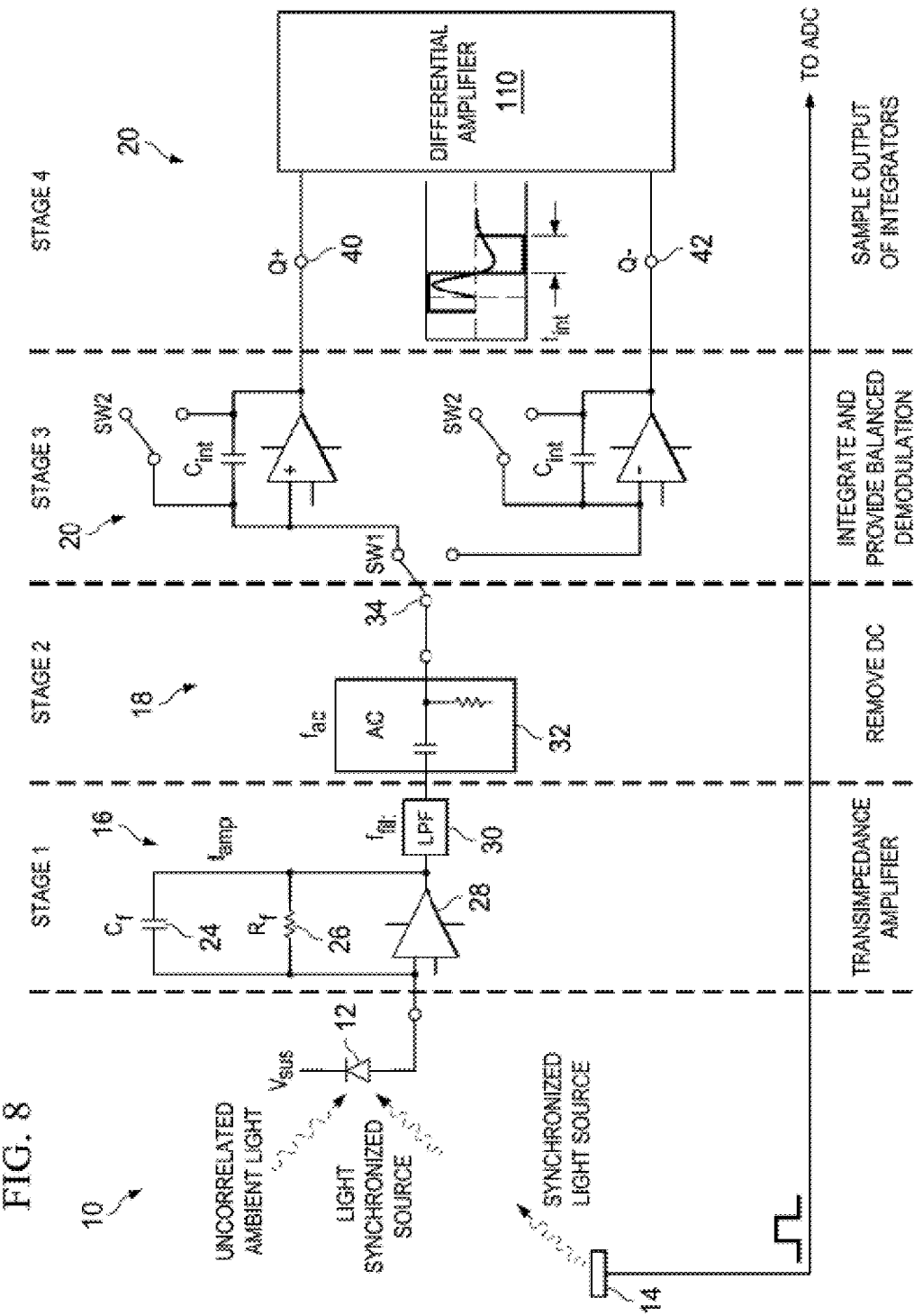

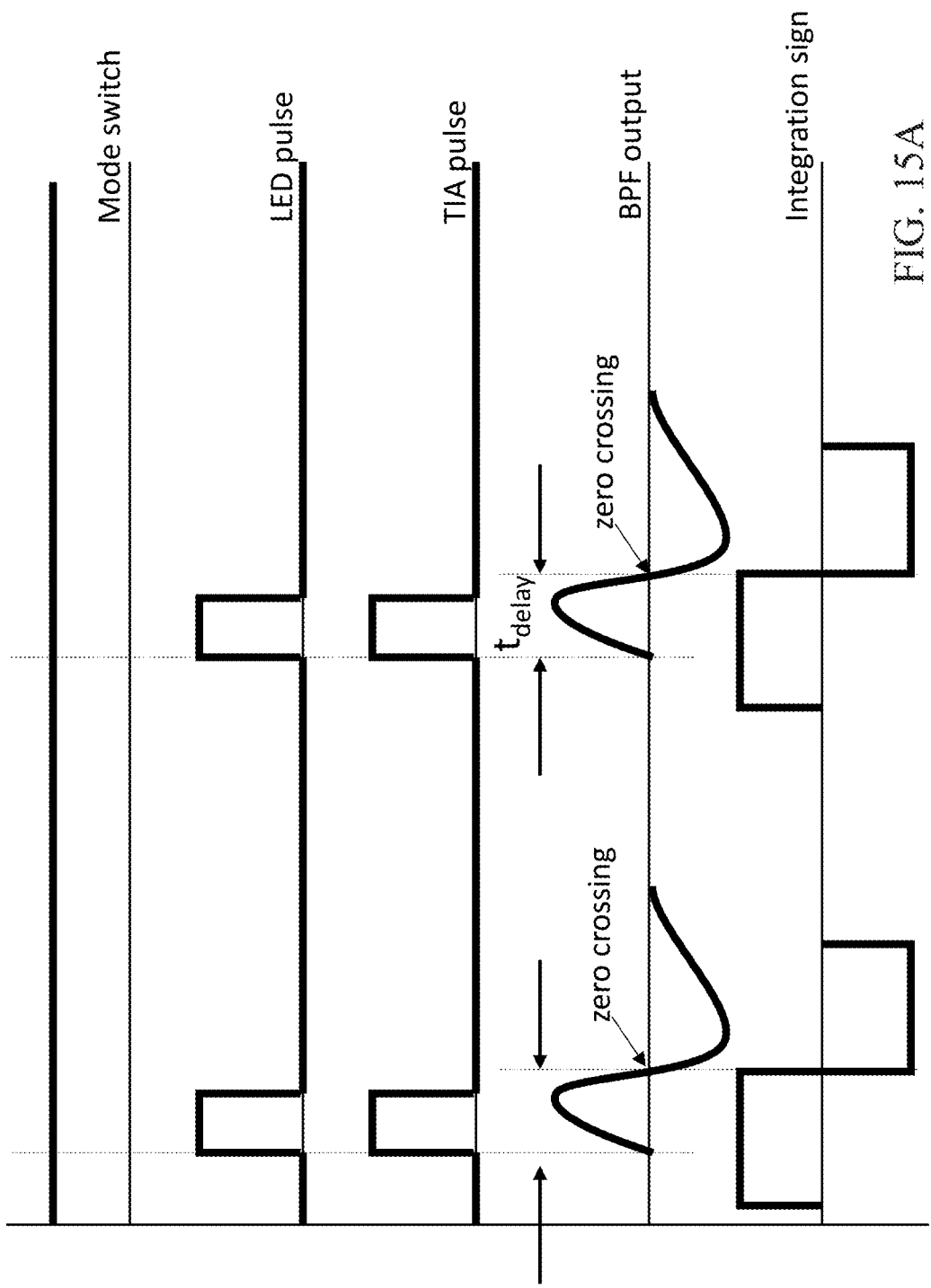

FIG. 16

| Mode | Switch | Application |
|---|---|---|
| Measure pulsed LED light (direct or reflected) | Keep switch connected to the amps | Measure LED light, reject ambient light |
| Measure ambient light | Open switch for a time T; integrate charge on PD; close switch to read the charge | Measure ambient light. Long integration time allows small light currents to be measured |
| Measure strong ambient light | Pulse switch for a short time to make a current pulse into the amplifier. | |
| Measure pulsed LED with a higher SNR | Combine mode 1 and mode 2 | More useful in low ambient light condition. |

CIRCUIT ARCHITECTURE FOR MODE SWITCH

CROSS-REFERENCE TO RELATED APPLICATIONS

This application claims the benefit of and priority from U.S. Provisional Patent Application Ser. No. 62/029,361 filed 25 Jul. 2014 entitled "Circuit Architecture for Mode Switch", which is incorporated herein by reference in its entirety.

TECHNICAL FIELD OF THE DISCLOSURE

The present disclosure relates to the field of integrated circuits, in particular to current detectors.

BACKGROUND

A photodiode (also referred to as "photodetector") is a type of a sensor capable of converting light into current or voltage. Generally, the photodiode is a semiconductor device with a PIN or PN connection structure. When a photon of sufficient energy strikes the photodiode, it excites electrons, creating free electrons and positively charged electron holes. The holes move toward the anode, and electrons toward the cathode, and a photocurrent is produced proportional to the amount of incident light on the photodiode.

Other types of sensors include e.g. pyro-electric, piezo-electric, or capacitive sensors.

All of these sensors are common in that they include a pair of electrodes and, when stimulated by their respective stimuli, the state of charge across the electrodes changes. Current resulting from the changed state of charge across the electrodes can then be used to detect and quantify the stimuli. For example, a photodiode produces a change in the state of charge across its electrodes when the light is incident on the photodiode. In other words, the photodiode generates current (which may be referred to as "photocurrent") in the presence of light, where the current is proportional to the amount of light incident on the photodiode. Similarly, a pyro-electric sensor produces a change in the state of charge across its electrodes when heated or cooled, a piezo-electric sensor produces a change in the state of charge across its electrodes in response to the change in its mechanical orientation (e.g. strain), while a capacitive sensor is one where changes in the environment change the effective capacitance of the sense element, which in turn changes the capacity to hold charge.

For such sensors, as well as other sensors operating according to similar principles of detecting change of charge state, it may be desirable to be able to detect and quantify stimuli originating from a specific source of interest as well as stimuli originating from all other sources besides the source of interest. For example, in context of a photodiode, it may be desirable to detect and quantify a contribution to the current generated by the photodiode that is due to the detection of light generated by a particular light source of interest, e.g. a particular light emitting diode (LED), as well as to detect and quantify contribution to the photocurrent that is due to the detection of light generated by all other light sources besides this light source of interest.

Overview

Present disclosure relates to a current detection module capable of differentiating and quantifying contribution to a current signal generated by a sensor as a result of stimulation by a certain source of interest (target source) from contributions from sources other than the source of interest (ambient sources). As long as the contribution from the target source comprises a pulsed signal, the module synchronizes itself to the pulse(s) so that there is a predetermined phase relationship between the pulse(s) and functions carried out by various stages of the module. The module may be re-used to also provide high precision detection and quantification of contributions to the sensor-generated current signal from ambient sources by presenting, to the current detection module, the contributions from ambient sources as one or more pulses which, in turn, trigger synchronization of the module. To that end, a detection system is provided that implements the current detection module as described herein and allows mode switching where, depending on the mode of operation being selected, the current detection module is configured to perform different kinds of measurements.

Accordingly, in one aspect of the present disclosure, a detection system includes a sensor configured to generate a current signal, where the current signal includes at least a first portion comprising a contribution to the current signal from a predefined source (i.e. a source of interest) and/or a second portion comprising a contribution to the current signal from one or more sources other than the predefined source, such other sources referred to herein as "ambient sources." The detection system further includes a current detection module configured to receive the current signal generated by the sensor and generate a digital value indicative of the first portion of the current signal and/or a digital value indicative of the second portion of the current signal.

Furthermore, the detection system also includes a mode switch configured to set the current detection module to operate in at least one of a first mode, a second mode, and a third mode. In the first mode, the current detection module is synchronized to the predefined source and is configured to generate the digital value indicative of the first portion (i.e. current detection module is configured to detect the contribution to the current signal from the source of interest, while cancelling, reducing, or rendering below the noise of the current detection module the contribution to the current signal from sources other than the source of interest). In the second mode, the current detection module is configured to generate the digital value indicative of at least the second portion (i.e. the current detection module is configured to only detect the contribution to the current signal from the ambient sources) when the contribution to the current signal from the one or more sources other than the predefined source is in a first range of values. In the third mode, the current detection module is configured to generate the digital value indicative of at least the second portion (i.e. the current detection module is configured to only detect the contribution to the current signal from the ambient sources) when the contribution to the current signal from the one or more sources other than the predefined source is in a second range of values, the second range of values having an upper end higher than an upper end of the first range of values (i.e. ambient sources cause larger currents).

It should be noted that, in various embodiments, both the first and second portion need not always be present (e.g. the source of interest may be off, or there may be no or negligible amount of contributions from the ambient sources), and, if both present, not always do both need to be measured. Furthermore, in some embodiments of the second and third modes, the current detection module may be configured to generate the digital value indicative of not only the second portion but also the first portion (i.e. the current detection module is configured to detect the contribution to the current signal both from the source of interest and ambient sources).

As will be appreciated by one skilled in the art, aspects of the present disclosure may be embodied in various manners—e.g. as a method, a system, a computer program product, or a computer-readable storage medium. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Functions described in this disclosure may be implemented as an algorithm executed by one or more processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems (e.g. to the existing current detection modules or controllers of such modules, etc.) or be stored upon manufacturing of these devices and systems.

Other features and advantages of the disclosure are apparent from the following description, and from the claims.

BRIEF DESCRIPTION OF THE DRAWING

To provide a more complete understanding of the present disclosure and features and advantages thereof, reference is made to the following description, taken in conjunction with the accompanying figures, wherein like reference numerals represent like parts, in which:

FIG. 4 is a simplified diagram of yet other example details of measurements associated with the circuit architecture, according to some embodiments of the disclosure;

FIG. 5 is a simplified diagram of an example detail of an application associated with the circuit architecture, according to some embodiments of the disclosure;

FIG. 6 is a simplified block diagram of another embodiment of the circuit architecture;

FIG. 7 is a simplified block diagram of example details of an application of an embodiment of the circuit architecture, according to some embodiments of the disclosure; and FIG. 8 is a simplified circuit diagram of another embodiment of the circuit architecture;

FIGS. 15A-15D show timing diagrams of four modes of operation of the detection system with mode switching, according to some embodiments of the disclosure; and FIG. 16 is a table summarizing four modes of operation of the detection system with mode switching, according to some embodiments of the disclosure.

DESCRIPTION OF EXAMPLE EMBODIMENTS OF THE DISCLOSURE

Exemplary Current Detection Module

Figure 1:
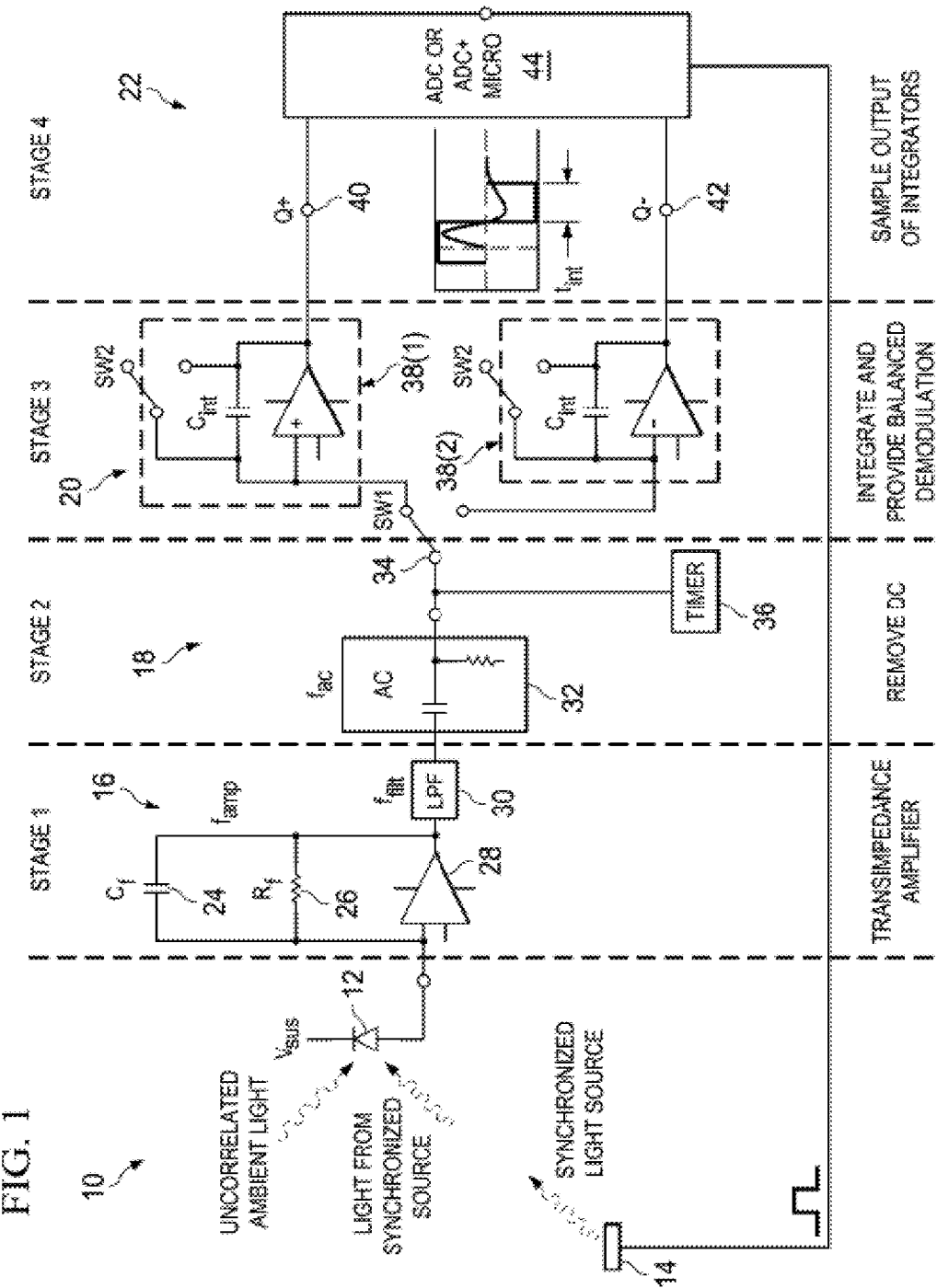
FIG. 1 is a simplified circuit diagram of a circuit architecture for a current detection module, according to some embodiments of the disclosure.

Embodiments of the present disclosure are based on the use of a current detection module capable of differentiating and quantifying (i.e. measuring) the contribution to the current signal generated by a certain source of interest from contributions from sources other than the predefined source of interest, i.e. ambient sources. As long as the contribution to the current signal from the predefined source comprises a pulsed signal (referred to in the following as "pulse(s) of interest"), the current detection module is configured to synchronize itself to the pulse(s) so that there is a predetermined phase relationship between the pulse(s) and functions carried out by various stages of the current detection module (referred to in the following as a "receiver circuit"). The pulsed signal of the source of interest may include one pulse or multiple pulses, where a pulse may include one or more frequency components. Ambient sources may also contain multiple frequency components, possibly even the same components as those of the pulse of the predefined source of interest. Because the frequencies present in the pulse(s) of interest are synchronized to the receiver circuit (i.e. synchronized to the clock of the current detection module), there is a certain known phase relationship between the current detection module and each of the frequency components of the pulse of interest (which phase relationship could be different for different frequencies in the pulse of interest, but nevertheless known ahead of time). The current detection module is designed to detect pulses synchronously and in a way that requires precise phase relationship between the receiver circuit and the source of interest. While the ambient sources may contain the same frequency components as the source of interest, the ambient sources are unlikely to contain precisely the same amplitudes and phases that make up the pulses of interest (i.e. ambient sources are unlikely to be synchronized to the current detection module). As a result, frequencies present in the ambient are averaged out even if the ambient sources contain very similar or the same frequencies as the pulse of interest.

Much of prior art approaches where it is desired to detect and measure contribution from a predefined source of interest from all other possible sources is based on avoiding interference with the ambient source by choosing a frequency of the source of interest to be different than the frequencies present in the ambient. Inventors of the present application realized that such approaches are not always successful because the content of the ambient is often unpredictable. Inventors of the present application further realized that by synchronizing the receiver circuit to the pulses of the signal of interest, it is possible to detect and measure contributions from the source of interest in presence of contributions from one or more ambient sources without having to choose frequencies for the pulses of the signal of interest that are different from the ambient (i.e. the frequency components could be the same).

An exemplary current detection module and functionality of such a module is now described in greater detail with reference to measurement of photocurrent signal generated by a photodiode in response to detecting light from a light source (i.e. for the example that the current detection module is used to detect photocurrent). However, teachings provided herein are equally applicable to current detection modules configured to detect currents generated by sensors, or charge generators, other than photodiodes, such as, but not limited to, pyro-electric, piezo-electric, or capacitive sensors. For all of these sensors (i.e. some kind of charge generators), a general setting described below for photodiodes is applicable where a sensor generates a current signal that may contain contributions from what may be considered as two "sources." One "source" is a particular source of interest (i.e. the sensor sensing some event of interest—e.g. light generated by a particular LED as detected by a photodiode, change in temperature due to a particular source of interest detected by a pyro-electric sensor, mechanical deformation caused by a particular force/source of interest as detected by a piezo-electric sensor, touch by e.g. a human or a stylus as detected by a capacitance sensor, etc.). The other "source" may be considered to include everything else besides the source of interest that may cause the change in the charge state of the sensor. Such a source is referred to as an "ambient source." In other words, the same sensor that senses contributions from the source of interest may also (or instead of, in case the source of interest is not providing any contribution) sense other things—e.g. the photodiode may detect ambient light, the capacitance sensor may sense touch that is not by a human or a stylus, etc. One common goal for all of these sensors may be to be able to distinguish and quantify these separate contributions to the current generated by the sensors.

Referring now to the example of a photodiode as a sensor, some embodiments of the present disclosure provide for measurement of photocurrent signal from a light source, which may be synchronized (e.g., specifically modulated).

Common photodiode circuits (e.g., photodiode amplifiers) are typically configured for one of low noise, wide bandwidth, and high dynamic range. Such circuits do not generally provide all three characteristics (low noise, wide bandwidth, and high dynamic range) simultaneously. Even if some circuits do provide all three characteristics, such circuits may require high power, or may not provide for high signal extraction of a target light source (especially in the presence of a high amount of ambient light, which is considered an interference and acts like noise), or may not be flexible to accommodate different sampling modes or multiple channels.

For example, Burr Brown's OPT201 integrated photodiode and amplifier provides low noise operation, but does not have any means to distinguish between different types of light sources. In another example, New Focus Inc.'s 1601 and 1611 high-speed photo-receivers have large gain bandwidth (GBW), low noise, high drive capability and large dynamic range to enable wide bandwidth low-noise detection of signals distributed over fiber-optic cables, or found in applications such as high resolution spectroscopy, fiber-optic sensors, and optical metrology. The photo-receivers consist of a silicon or InGaAs PIN photodiode followed by a low-noise amplifier. However, these photo-receives are not capable of sampling multiple channels, and are designed such that there is no need to distinguish between different types of light that fall on the sensor—predefined source of interest and the ambient.

Turning to FIG. 1, FIG. 1 is a simplified block diagram of electrical circuit 10 that may be used as a current detection module described herein. Electrical circuit 10 is configured to simultaneously provide low-noise and low-power consumption (among other features) while avoiding interference from uncorrelated sources besides the source of interest (for the example of a sensor being a photodiode, such uncorrelated sources being e.g., sunlight, background light, ambient light) in the environment. Furthermore, the circuit architecture is configured to have high dynamic range that is suitable for use in the presence of a strong ambient source, such as e.g. sunlight, for the example of a sensor being a photodiode. The circuit architecture can be extended to multiple channels, for example, in applications that involve reading multiple sensor (e.g. multiple photodiode) signals concurrently.

According to various embodiments, electrical circuit 10 can provide the following features substantially simultaneously: low noise, high dynamic range, high rejection of uncorrelated ambient sources, high signal extraction of a locked or target source (i.e. the source of interest), low power operation, and flexibility for different sampling modes. Furthermore, electrical circuit 10 can allow for simultaneous sampling of multiple channels for analog-to-digital conversion, improve ambient signal rejection in the first mode, and measure ambient signal in the second mode. One example is ambient light rejection (ALR) in the first mode when a sensor is a photodiode. Multiple channels are serviced by a single and often more precise analog-to-digital converters (ADCs) while maintaining simultaneous measurement on all channels.

According to a specific embodiment, electrical circuit 10 may comprise a sensor 12 that detects a stimuli from a target source of interest 14, e.g. a photodiode 12 that receives light from a light source 14. The current signal generated by the sensor 12 can include a single pulse of low duty cycle or a multiple pulse train of low duty cycle (e.g., depending on the duty cycle of target source 14). In some embodiments, the target source 14 may be modulated by an integrated circuit (not shown) coupled to electrical circuit 10.

According to various embodiments, electrical circuit 10 can comprise four stages 16, 18, 20, and 22. Stage 16 can include a trans-impedance amplifier (TIA), which may amplify the current signal from the sensor 12 and generate a low noise signal. The trans-impedance amplifier can also convert the current signal to a voltage at the output. Stage 16 includes a feedback capacitance 24 (CO in parallel with a feedback resistor 26 ($R_f$) connected to an operational amplifier (op-amp) 28 in an R-C feedback loop, for example, to reduce noise and stabilize the circuit.

Any source of interest 14 (including DC source, e.g. DC light for the example of a sensor being a photodiode) whose bandwidth is within the amplifier bandwidth may be amplified by amplifier 28. Generally, capacitance of a sensor can affect noise gain based on the relative value of the capacitance to resistance value $R_f$ of feedback resistor 26 and capacitance value $C_f$ of feedback capacitor 24. Configuring stage 16 as a first stage can provide increased flexibility to minimize excess noise gain. In a general sense, two dominant noise sources in electrical circuit 10 include Johnson noise of feedback resistor 26 and amplifier 28's input voltage noise. To reduce Johnson noise, resistance value $R_f$ of feedback resistor 26 can be chosen to be as large as possible consistent with the largest DC current that is expected for a given arrangement of sensor 12 and other components. Such a configuration may provide minimum amplifier noise consistent with the total DC current. Capacitance value $C_f$ of feedback capacitor 24 can be chosen to change the bandwidth of the current signal (which may be of the order of approximately $1/\tau$, where $\tau$ refers to the input pulse duration) as desired. Stage 16 can also include a low pass filter (LPF) 30 that additionally filters out high frequency noise in the photocurrent signal. LPF 30 can also increase the duration of pulses of the current signal generated by sensor 12 (which may coincide with the pulse duration of the (synchronized) target source 14). The frequency threshold of LPF 30 can be configured as desired based on particular needs depending on the expected (or measured) noise characteristics.

Stage 18 may comprise a high pass filter, active or passive, with frequency $f_{ac}$, and a capacitor that provides AC coupling. Stage 18 can eliminate low frequencies (e.g., remove DC) and allow high gain to be provided in subsequent stages. The pulsed output from the stage 16 is filtered by having low frequency components removed by stage 18, thereby providing a zero cross-over point where the amplitude of the current signal changes from positive to negative. Stage 18 can eliminate some of the noise components from stage 16 and high frequency noise and lower frequency currents from ambient signal (e.g. ambient light) or uncorrelated ambient sources.

In some embodiments, a square pulse shaped signal from target source 14 may be modified by the filtering action of LPF 30 and stage 18 to eliminate low frequencies. The corner frequencies (e.g., boundary in the frequency response at which energy flowing through begins to reduce (attenuate or reflect)) of stages 16 and 18 may be chosen to maximize signal measurement and provide ALR. For example, the corner frequency of the high pass filter of stage 18 can be set as large as $0.5/\tau$. The choice can also be influenced by the integration time chosen in next stage 20.

Stage 20 may comprise integration and demodulation. A single pole changeover switch 34 may switch the incoming signal based on a clock from timer 36. The clock cycle of timer 36 may be configured to match the zero cross-over point of the photocurrent signal from stage 18. When the zero cross-over point occurs, switch 34 may switch from integrating amplifier 38(1) to integrating amplifier 38(2). Two integrating amplifiers 38(1) and 38(2) may be used to integrate in succession on the positive portion of the signal from stage 18 when switch 34 is connected to the positive integrating amplifier 38(1) and on the negative portion of the signal from stage 18 when switch 34 is connected to the negative integrating amplifier 38(2). Each of positive integrating amplifier 38(1) and negative integrating amplifier 38(2) may include a capacitor $C_{int}$ configured to enable the operational amplifier therein to operate as an integrator. In some embodiments, switches SW2 may be used to reset positive integrating amplifier 38(1) and negative integrating amplifier 38(2), for example, after every conversion cycle or after multiple integration phases.

Each of positive integrating amplifier 38(1) and negative integrating amplifier 38(2) (generally referred to individually as an "integrator" 38) acts like a storage element that produces an output voltage output proportional to the integral of its input current (converted from voltage output of the previous stage) over time. In other words, the magnitude of the output voltage is determined by the length of time (integration period $t_{int}$) during which an input voltage is present as the current through the feedback loop (comprising $C_{int}$) charges or discharges capacitor $C_{int}$. The circuit operates by passing a current that charges capacitor $C_{int}$ over time from the input current of stage 18. When the input current of stage 18 is firstly applied to the integrator, the feedback capacitor $C_{int}$ begins to charge and the output voltage is determined by the total charge (which is the integral of the input current over time).

Positive integrating amplifier 38(1) may generate a positive integrated value 40 ($Q_+$), which is the integral over time of the positive amplitude of the alternating current signal from stage 18, and negative integrating amplifier 38(2) may generate a negative integrated value 42 ($Q_-$), which is the integral over time of the negative amplitude of the alternating current signal from stage 18. The integration period $t_{int}$ can be configured over a wide range based on particular needs. The start of the integration cycle may be controlled by timer 36 in a microcomputer, a simple programmable circuit, or other suitable component. The gain of the amplifier can be chosen to optimize conversion by an analog-to-digital convertor (ADC) 44 (as DC and low frequency components of ambient light are largely removed after stage 18) at stage 22. At the end of the positive and negative integration cycle, substantially all currents in the integration period $t_{int}$ may be integrated and the voltage may be held at the outputs of stage 20. The voltages may be subtracted either before conversion by a difference amplifier or converted by ADC 44 and then subtracted digitally.

Mathematically, the integration and subtraction are similar to a low pass filter and a "lock-in" filter to further remove noise artifacts of the ambient sources while amplifying the current signal. For example, the phase of switch 34 can be adjusted to provide "lock-in" functionality to a signal originating from a distant system. Assume, merely for illustrative purposes, and not as a limitation, that a distant light source produces a train of N pulses repeating at a rate R. Timer 36 can be configured to lock to the phase of the clock that generates the N pulses. Thus a phase lock loop can be constructed to measure the light intensity of the distant light source. Positive integrating amplifier 38(1) and negative integrating amplifier 38(2) can together provide increased ALR. Outputs 40 and 42 may be fed to ADC (or ADC integrated with a micro-controller) 44 at stage 22 to perform further operations.

ADC 44 can read the output voltage of stage 20 and a controller therein can reset integrators 38(1) and 38(2), for example, by momentarily closing SW2, to start a new integration cycle. The reset can occur at the end of each pulse or at the end of a group of pulses. The voltage at stage 20 may represent a signal charge deposited at the sensor 12 as a result of detecting stimuli from the target source 14 in addition to charge from substantially all ambient interference. In an example embodiment, the pulses may be added together thereby increasing signal strength and reducing noise and interference digitally after ADC 44. In another example embodiment, the pulses may be added in an analog domain until SW2 resets integrating capacitors $C_{int}$. Embodiments of electrical circuit 10 can permit extension of the circuit architecture to ultra short pulses, for example in nanosecond and picosecond domain, without substantially increasing the speed of ADC 44. High dynamic range may be facilitated as digital additions of pulses can be carried out over many more pulses, almost without limit, than any analog addition on the integrating capacitors $C_{int}$ would permit.

According to various embodiments, input current generated by sensor 12 may be converted to voltage at stage 16.

Any frequency content of the voltage signal may be shaped by the band pass filtering functions at state 18. The output voltage of stage 18 may be converted back to current, for example, using a suitable resistor, and integrated with capacitor $C_{int}$ over time $t_{int}$ over positive and negative cycles. At least a portion of the behavior of electrical circuit 10 may be indicated by the following equations:

$$V_{TIA} = i_p \times R_f$$

$$V_{ac} = BPF(f_{filt}) \times V_{TIA}$$

$$V_{int} = \left(\frac{V_{ac}}{R_{in}}\right) \times (C_{int} \times t_{int})$$

where $V_{TIA}$ is the output voltage at stage 16; $i_p$ is the current from sensor 12 (e.g. photovoltaic current for the example of sensor 12 being a photodiode); $R_f$ is the resistance of feedback resistor 26; $V_{ac}$ is the output voltage at stage 18; $BPF(f_{filt})$ is a bandpass filter shaping function of stage 18; $V_{int}$ is the output voltage at stage 20; $R_{in}$ is the resistance of a resistor (not shown) at stage 20; $C_{int}$ is the capacitance at stage 20; and $t_{int}$ is the integration time.

For example, Rf may be chosen to prevent saturation at stage 16 with a high amount of low frequency ambient sources, such as e.g. sunlight. The corner frequencies can be chosen to minimize interference while transmitting most of the signal pulse at stage 18. Moreover, the choice of $R_{in}$ and $C_{int}$ can allow signal gain at stage 20 to match ADC input range at stage 22. Further, multiple cycles of analog integration over many pulses with digital integration at ADC 44 can allow a large dynamic range.

In some embodiments, an intense short pulse produced by target source 14 may perform better for low power operation as the system of amplifiers and ADC can be powered down between the pulses. Also, for the same net power consumed by synchronous target source 14, signal-to-noise-ratio (SNR) can be maximized by using the shortest possible pulse that can be produced by a driver circuit. (The shortest possible pulse may be limited by the peak current output available.) Electrical circuit 10 may be dynamically or programmatically configured in some embodiments, for example, by changing the $C_f$, $R_f$, $C_{int}$, and other passive component values and corner frequency values as desired.

In some embodiments, the low frequency (e.g., DC) component of the current signal generated by sensor 12 may be measured by directly connecting stage 16 to the input of ADC 44. Alternatively, the low frequency component may be measured by connecting stage 16 to either positive integrating amplifier 38(1) or negative integrating amplifier 38(2) of stage 20. In embodiments with low levels of ambient signals, one of positive and negative integrating amplifiers 38(1) and 38(2), respectively, may be connected directly to sensor 12, bypassing stages 16 and 18.

According to various embodiments, at least some components of stages 16, 18, and 20 are programmable (e.g., component values adjustable according to user specifications) after electrical circuit has been implemented in a physical form. The component values may be programmable manually, or by a suitable computing device or controller. For example, capacitance $C_f$ of feedback capacitor 24, resistance $R_f$ of feedback resistor 26; bandpass filter shaping function $BPF(f_{filt})$, resistance $R_{in}$, capacitance $C_{int}$ etc. can be programmed according to the application in which electrical circuit 10 is to be used. Thus, the same physical representation of electrical circuit 10 may have a first set of component values in one application (e.g., photoplethysmography (PPG) system used in controlled ambient light) and a different, second set of component values in a different application (e.g., wireless sensor used in uncontrolled ambient light).

Figure 2:
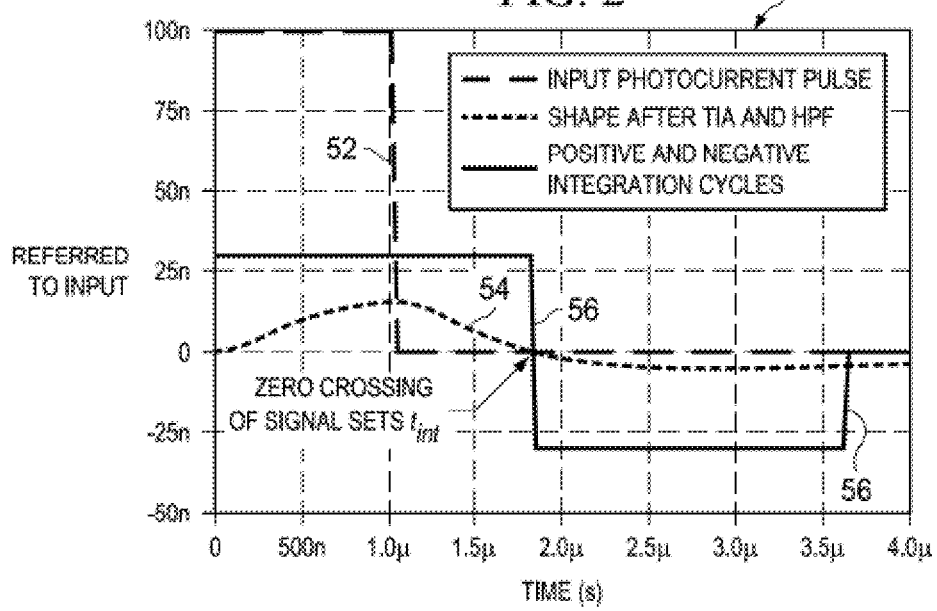
FIG. 2 is a simplified diagram illustrating example details of measurements associated with the circuit architecture, according to some embodiments of the disclosure.

Turning to FIG. 2, FIG. 2 is a simplified diagram illustrating an example signal chart 50 according to an embodiment of electrical circuit 10. Merely for example purposes, and not as a limitation, the pulse duration τ was set at 1 μs, and the high pass filter corner frequency (of stage 18) was set at 300 kHz or 0.3/τ. The output of the stages was referred to the input to allow for easy comparison. Input photocurrent pulse 52 from synchronized light source may result in a photocurrent signal 54, illustrated after stages 16 and 18. Signal 54 indicates an AC signal, with a zero cross-over point. The zero cross-over point may set the integrating cycle duration $t_{int}$. Positive and negative integration cycles may be denoted by a line 56, which also has a zero cross-over point coinciding with the zero cross-over point of signal 54.

Figure 3:
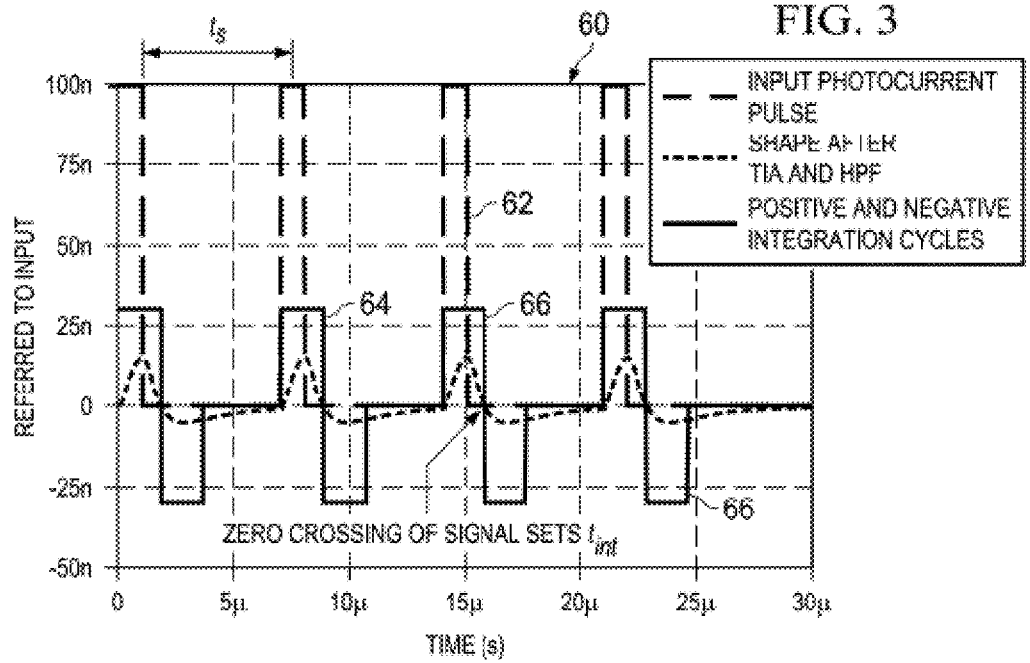
FIG. 3 is a simplified diagram of other example details of measurements associated with the circuit architecture, according to some embodiments of the disclosure.

Turning to FIG. 3, FIG. 3 is a simplified diagram illustrating an example signal chart 60 according to an embodiment of electrical circuit 10. Input photocurrent pulse 62 from synchronized light source may result in a photocurrent signal 64, illustrated after stages 16 and 18. Signal 64 is an AC signal, with a zero cross-over point. The zero cross-over point may set the integrating cycle duration $t_{int}$. Positive and negative integration cycles may be denoted by the line 66, which also has a zero cross-over point coinciding with the zero cross-over point of signal 64. Input photocurrent signal 62 may be generated as pulses (e.g., with a short 1 μs pulse). Each pulse of signal 64 may be shaped by the action of stages 16 and 18. Positive and negative integration cycles are applied to each pulse in the train of pulses. The separation $t_s$ between pulses may be configured based on the settling time or to minimize any effect of particularly dominant frequency components (if any) from ambient light.

Turning to FIG. 4, FIG. 4 is a simplified diagram illustrating a graph 80 showing input charge over frequency of interfering ambient light. Graph 80 illustrates the suppression of ambient light according to electrical circuit 10. Assume, merely for illustrative purposes, and not as a limitation, that a light source in the environment has a frequency f. Further assume that the phase of the ambient light is somehow synchronized to produce worst case interference at each possible frequency of the ambient light (indicated along the x-axis). The measured amplitude of the photocurrent signal produced at that frequency can be reduced by the action of all four stages 16, 18, 20 and 22. In the case of a train of multiple pulses, suppression may be increased even further.

Graph 80 was generated using 16 pulses, and the input referred integrated current (after stage 22) was calculated as charge on the Y-axis. According to embodiments of electrical circuit 10, ALR of almost a factor of 100 at frequencies below 50 kHz may be observed. Many ambient light sources such as fluorescent lamps and light emitting diode (LED) lights have components at low frequencies. Very low frequencies such as 120 Hz may be suppressed by factors exceeding 1000 and DC light may be completely blocked.

It may be noted that embodiments of electrical circuit 10 may reject electrical noise injected at sensor 12 similar to rejection of currents generated by ambient sources. Indeed, components of electrical circuit 10 may not distinguish between currents generated by the sensor in response to stimuli of ambient sources or electromagnetic interference (EMI) or any other electrical noise injected into the circuit, facilitating robustness in the presence of both electrical interference and interference due to detection by the sensor of ambient source (e.g. optical interference for the example of sensor 12 being a photodiode).

Turning to FIG. 5, FIG. 5 is a simplified diagram illustrating an example application 90 of electrical circuit 10 as used in a photoplethysmography system 92. A photoplethysmograph is a device used to optically measure changes in the effective light transmission or reflectance of an organ. Examples of photoplethysmography systems include pulse oximeters, cardiovascular monitors, and respiration detectors. Application 90 illustrated in the FIGURE can include a pulse oximeter, although electrical circuit 10 may be implemented in any other type of photoplethysmography systems as well, within the broad scope of the embodiments.

The pulse oximeter of application 90 may include photodiode 12 and synchronous light source (e.g., red and infrared light emitting LED) connected to photoplethysmography system 92, which can include electrical circuit 10 and other components, based on the particular application need. The pulse oximeter may be attached to, or otherwise placed in proximity with an organ (e.g., fingertip, wrist, etc.) 94 (e.g., of the patient whose pulse is being monitored). Light emitted by synchronous light source 14 may be partially reflected, transmitted, absorbed, and/or scattered by the organ (e.g., skin, surrounding tissues, and the blood at the fingertip) before it reaches photodiode 12. The photocurrent signal from photodiode 12 can provide a measurement of the organ, for example, indicative of pulse rate, or oxygen content, etc.

Currently available pulse oximeters and other photoplethysmography systems use caps, light proof enclosures, and other such devices to prevent ambient/background light from generating noise in the photoplethysmography systems. With electrical circuit 10, such light blocking enclosures (e.g., caps, boxes, etc.) need not be used, as electrical circuit 10 includes noise reduction capabilities sufficient to overcome ambient and other background light noise. Moreover, because of the noise reduction characteristics of electrical circuit 10, and its consequent reduced sensitivity to ambient and DC light, the distance between synchronous light source 14 and photodiode 12 may be configured based on convenience factors, rather than noise reduction.

Turning to FIG. 6, FIG. 6 is a simplified block diagram illustrating another embodiment of electrical circuit 10. Multiple (e.g., four) sensors 12, shown in FIG. 6 as photodiodes 12, may be connected to ADC 44, for example, to measure light intensity from four different spatial orientations. In some embodiments, each sensor 12 may be connected to separate stages 16, 18 and 20, with all sensors 12 sharing a common ADC 44. Each of stages 20 may provide a positive integrated value and a negative integrated value to ADC 44. ADC 44 may sample the outputs from a specific stage 20 before proceeding to the next stage 20, and so on, until it samples the outputs from substantially all stage 20 within a certain time interval. The time interval may be configured according to the power cycle of light source 14, such that ADC 44 completes sampling the outputs from all stage 20 before light source 14 powers down.

Moreover, the output from stage 20 can remain constant after the integration phase until reset, ADC 44 can be multiplexed to sample each of the outputs without compromising performance. Thus embodiments of electrical circuit 10 can allow a relatively lower cost low speed ADC with low frequency switching between channels can be used without compromising performance. Such circuit architecture can be used in specialized sensor applications, for example, that use lateral photodiodes, quad detectors, or optical angle sensors in context of a sensor being a photodiode. With the circuit architecture of embodiments of electrical circuit 19, pulse width of the input light and substantially all components of stages 16, 18, and 20 can be configured with nanosecond pulses without substantially affecting ADC 44's sample rate.

Turning to FIG. 7, FIG. 7 is a simplified diagram illustrating an example application 100 of electrical circuit 10. Smartphone 102 may be configured to detect gestures of a user 104 based on optical signals (rather than touch). Multiple photodiodes 12 may be configured on Smartphone 102 (e.g., on its display screen). Synchronous light source 14 may be provided on Smartphone 102 in some embodiments. Light from light source 14 may be reflected off user 104, and may be measured by photodiodes 12. The amount of light arriving at each photodiode 12 may depend on the particular gesture (hand, finger or body position) of user 104. When user 104 changes the gesture, the amount of light on photodiodes 12 may also change. This change may be calculated by a suitably calibrated microcontroller to detect the gesture and derive a suitable meaning thereof. With electrical circuit 10 implemented in such application 100, the sensitivity of the system to the background light and other extraneous light may be reduced without compromising the performance.

Turning to FIG. 8, FIG. 8 is a simplified circuit diagram illustrating another example configuration of an embodiment of electrical circuit 10. Instead of ADC 44, a differential amplifier 110 may be used in stage 22. Differential amplifier 110 may compute a difference between outputs 40 and 42 and send the difference to ADC 44 or other suitable component (e.g., microprocessor, digital signal processor, etc.). Differential amplifier 110 may also amplify the difference in outputs 40 and 42, and thereby increase accuracy of measurement based on particular needs.

To summarize the above description, an example electrical circuit is provided and includes a sensor (e.g. a photodiode) that receives a signal (e.g. light signal) from a target source (e.g. a target light source) and generates a current signal (e.g. a photocurrent signal), a trans-impedance amplifier that amplifies the current signal and generates a low noise signal, and a high pass filter that converts the low noise signal into an AC signal having a positive amplitude, a negative amplitude, and a zero cross-over point between the positive amplitude and the negative amplitude. The electrical circuit also includes a positive integrating amplifier that receives the positive amplitude of the AC signal and generates a positive integrated value over an integration period, and a negative integrating amplifier that receives the negative amplitude of the AC signal and generates a negative integrated value over the integration period. The electrical circuit further includes at least one ADC that receives the positive and negative integrated values.

In a specific embodiment where the sensor is a photodiode, the electrical circuit is coupled to a photoplethysmography system. Light from the light source reflects off, or transmits through an organ before reaching the photodiode, such that the photocurrent signal from the photodiode can provide an indication of a measurement of the organ. The photoplethysmography system does not have to include a light blocking enclosure to keep out ambient light for accurate measurements.

A system is also provided that includes a plurality of sensors (e.g. photodiodes) that receive one or more signals from one or more target sources (e.g. light sources), with each one of the sensors generating a current signal, a plurality of trans-impedance amplifiers, in which each trans-impedance amplifier amplifies the current signal from one of the sensors and generates a low noise signal, a plurality of high pass filters, in which each high pass filter converts the low noise signal from each trans-impedance amplifier into an AC signal having a positive amplitude, a negative amplitude, and a zero cross-over point between the positive amplitude and the negative amplitude and a plurality of integrators. Each integrator includes a positive integrating amplifier that receives the positive amplitude of the AC signal from each high pass filter and generates a positive integrated value over an integration period, and a negative integrating amplifier that receives the negative amplitude of the AC signal from each high pass filter and generates a negative integrated value over the integration period. The system further includes an ADC that receives the positive and negative integrated values from the plurality of integrators.

Using Current Detection Module with Mode Switching

Embodiments of the present disclosure are further based on the recognition that a current detection module as described above may be re-used to not only detect and quantify contribution to the current signal from a predefined, target, source of interest, but also provide high precision detection and quantification of contributions to the sensor-generated current signal from sources other than the predefined source. To that end, a detection system is provided that implements the current detection module as described above and further allows mode switching where, depending on the mode of operation being selected, the current detection module is configured to perform different kinds of measurements.

Figure 9:
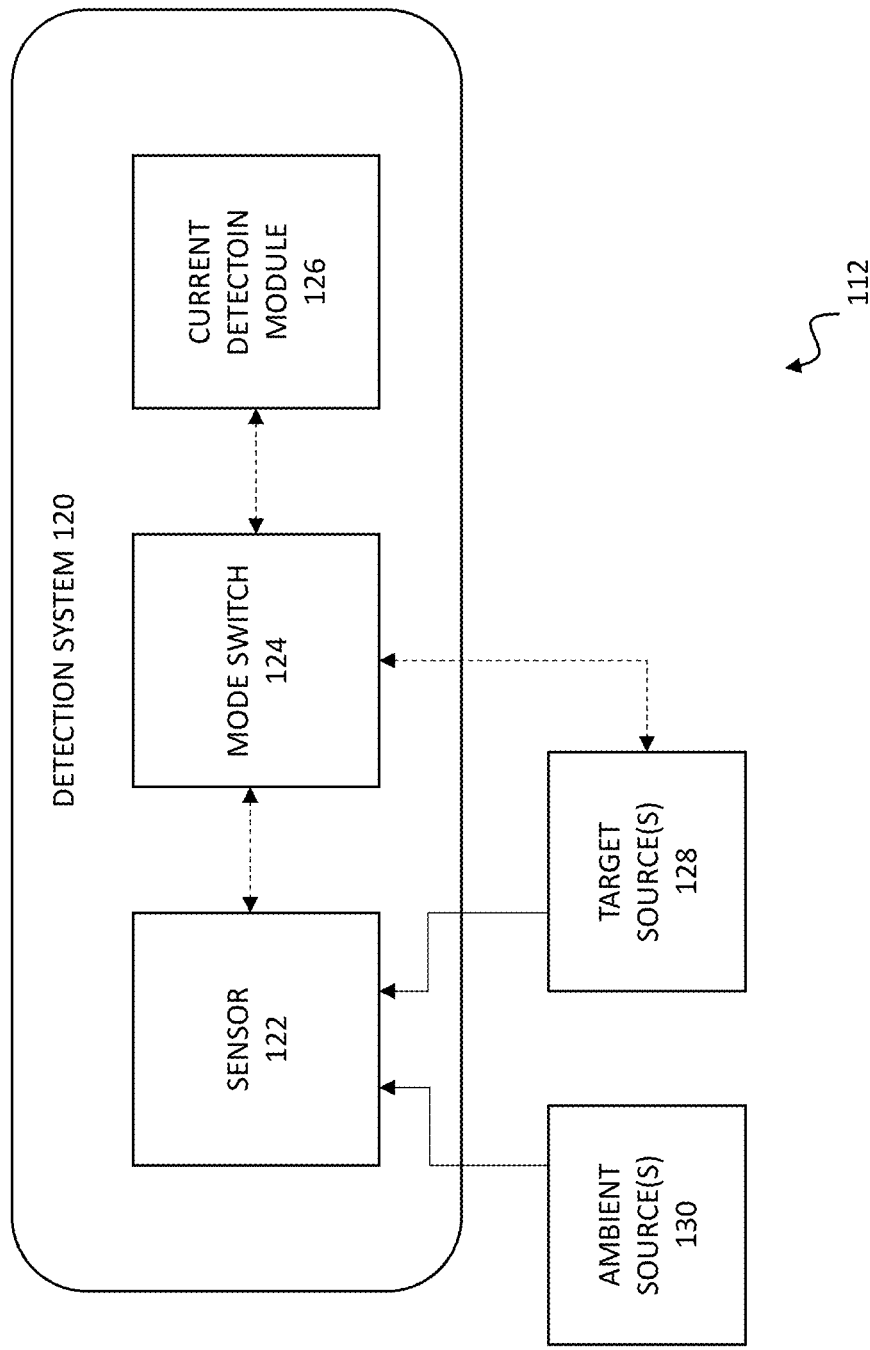
FIG. 9 is a simplified diagram of a detection system with mode switching, according to some embodiments of the disclosure.

FIG. 9 is a simplified diagram of an architecture 112 for use of detection system 120 with mode switching, according to some embodiments of the disclosure. As shown, detection system 120 may include sensor 122, a mode switch 124, and a current detection module 126.

Current detection module 126 could be implemented as electrical circuit 10 described above.

Figure 10:
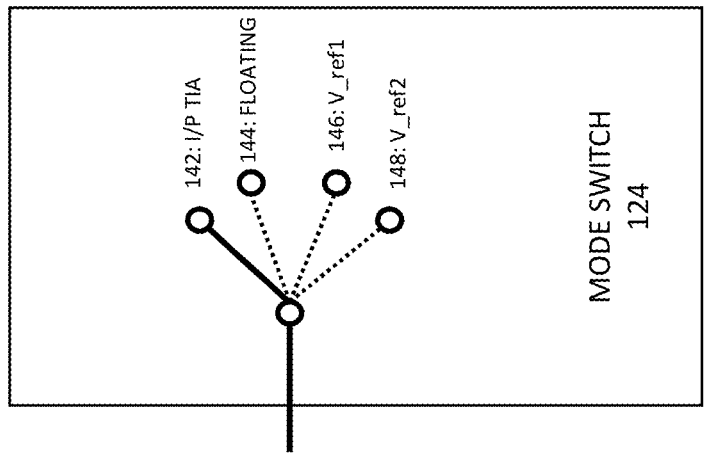
FIG. 10 is a simplified diagram of a sensor, according to some embodiments of the disclosure.

Sensor 122 could be implemented as sensor 12 described above, which could be e.g. a photodiode, a pyro-electric sensor, a piezo-electric sensor, or a capacitive sensor. In general, sensor 122 may be considered to be a device comprising one or more charge collecting/generating capacitive elements, as shown in FIG. 10. As used herein, the term "capacitive elements" of a sensor refer to elements of a sensor capable of holding a certain charge or, in other words, possessing a certain capacitance. Such capacitive elements may include capacitors built into the sensor on purpose, shown in FIG. 10 with one or more designated capacitive elements 132, as well as capacitances that a sensor may intrinsically possess without being included on purpose (i.e. "parasitic capacitances" that may be built into the sensor itself and/or happen to be in the circuit elements surrounding the sensor), such parasitic elements schematically illustrated in FIG. 10 as parasitic capacitive elements 134.

Sensor 122 is configured to detect stimuli, shown in FIG. 9 with arrows going to sensor 122, which could originate from one or more sources of interest, shown as "target source 128" in FIG. 9, and/or from one or more sources which may comprise any sources that are not classified as the target sources, shown as "ambient source 130" in FIG. 9. Target source 128 could be implemented as source 14 described above, while ambient source 130 could e.g. include various sources contributing to ambient light (i.e. what is referred to as "ambient source 130" does not have to be a single, definitive source, but could include any kind of stimuli generator that a particular sensor 122 could detect).

Mode switch 124 is configured to control operation of current detection module 126 in order to use the same current detection module 126 to perform different measurements in the following modes. In each of what is referred to as a "first mode" and a "fourth mode" described herein, current detection module 126 is configured to detect contribution from the source of interest 128. The first and fourth modes differ in how exactly such contribution is detected. In each of what is referred to as a "second mode" and a "third mode" described herein, current detection module 126 is configured to detect contribution from the ambient source 130. The second and third modes differ in which ranges of signal intensity generated by ambient source 130 may be correctly measured. In particular, the second mode may be used to detect contributions from ambient sources is in a certain first range of amplitudes, while the third mode may be used to detect contribution in a higher range of amplitudes (which amplitudes could oversaturate sensor 122 resulting in incorrect measurement if measured in the second mode). In order to control different modes of operation, mode switch 124 may be configured to ensure that one or more of sensor 122, current detection module 126, and target source 128 are synchronized (which synchronization is described in more detail below), as shown in FIG. 9 with dashed arrows between mode switch 124 and each one of these elements.

In various embodiments, functionality provided by mode switch 124 may be implemented different manners—e.g. in software, hardware, a combination of software and hardware, etc.

Figure 11:
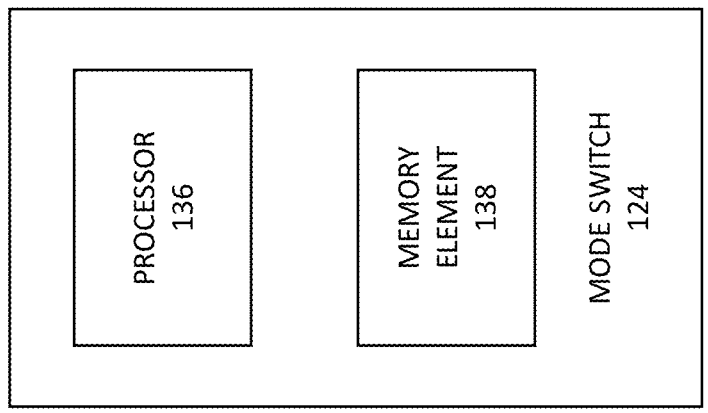
FIG. 11 is a simplified diagram of a mode switch, according to some embodiments of the disclosure.

FIG. 11 illustrates one example of implementing mode switch 124 in software. In such an embodiment, mode switch 124 may include at least one processor 136 and at least one memory element 138, along with any other suitable hardware and/or software to enable its intended functionality. Mode switch 124 may be considered to include one or more modules (not shown in FIG. 11) configured to carry out functionality described herein related to mode switching and synchronization, as well as an interface (not shown in FIG. 11) to enable communication with other devices, e.g. sensor 122, current detection module 126, and target source 128 illustrated in FIG. 9. As a result of performing functionality described herein, mode switch 124 can ensure that current detection module 126 properly performs measurements in one of the modes. Optionally, in different embodiments, various repositories (not shown in FIG. 11) may be associated with mode switch 124, including, but not limited to, e.g. a repository storing information related to target sources 128, a repository storing information indicative of specifications and limitations of sensor 122, etc.

Figure 12:
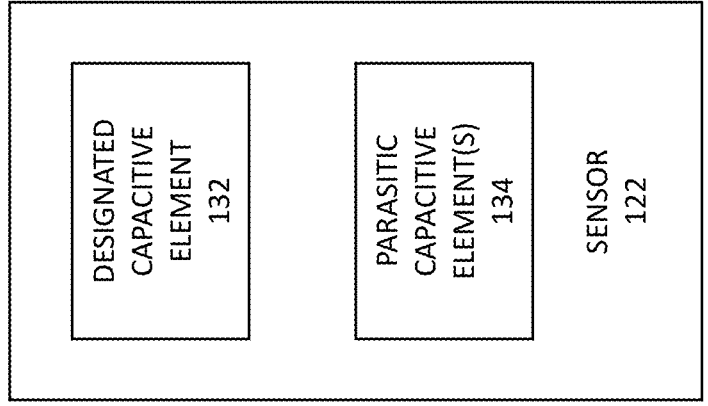
FIG. 12 is a simplified diagram a mode switch, according to other embodiments of the disclosure.

FIG. 12 illustrates one example of implementing mode switch 124 in hardware. In such implementation, mode switch 124 may be configured as an actual switch that could be in one of the following positions: position 142, where mode switch 124 connects the output of sensor 122 to the input of the first stage (i.e., the TIA) of current detection module 126 (i.e. as a result of sensor 122 receiving stimuli, current may flow from sensor 122 to current detection module 126); position 144, where mode switch 124 connects the output of sensor 122 is not connected to anything (i.e., because the output of sensor 122 is open, current cannot flow from sensor 122 and, as a result of receiving stimuli, sensor 122 accumulates charge, referred to as "floating" of sensor 122); or position 146 where mode switch 124 connects the output of sensor 122 to a predefined reference voltage, e.g.

to the common mode (CM) node of the TIA in the first stage of current detection module 126, or to some other reference voltage (i.e. irrespective of how much stimuli sensor 122 is receiving, sensor 122 is maintained to be at the reference voltage). In an optional embodiment, mode switch 124 could be configured to connect sensor 122 to at least two different reference voltages, shown as a first reference voltage V_ref1 in position 146 and a second reference voltage V_ref2 in position 148. In various embodiments, mode switch 124 may be implemented using any number of switches, connected in series or/and parallel, as suitable for a particular deployment of the detection system 120. In various embodiments, one or more switches of the mode switch 124 may be implemented as complementary metal-oxide-semiconductor (CMOS) switches.

Figure 13:
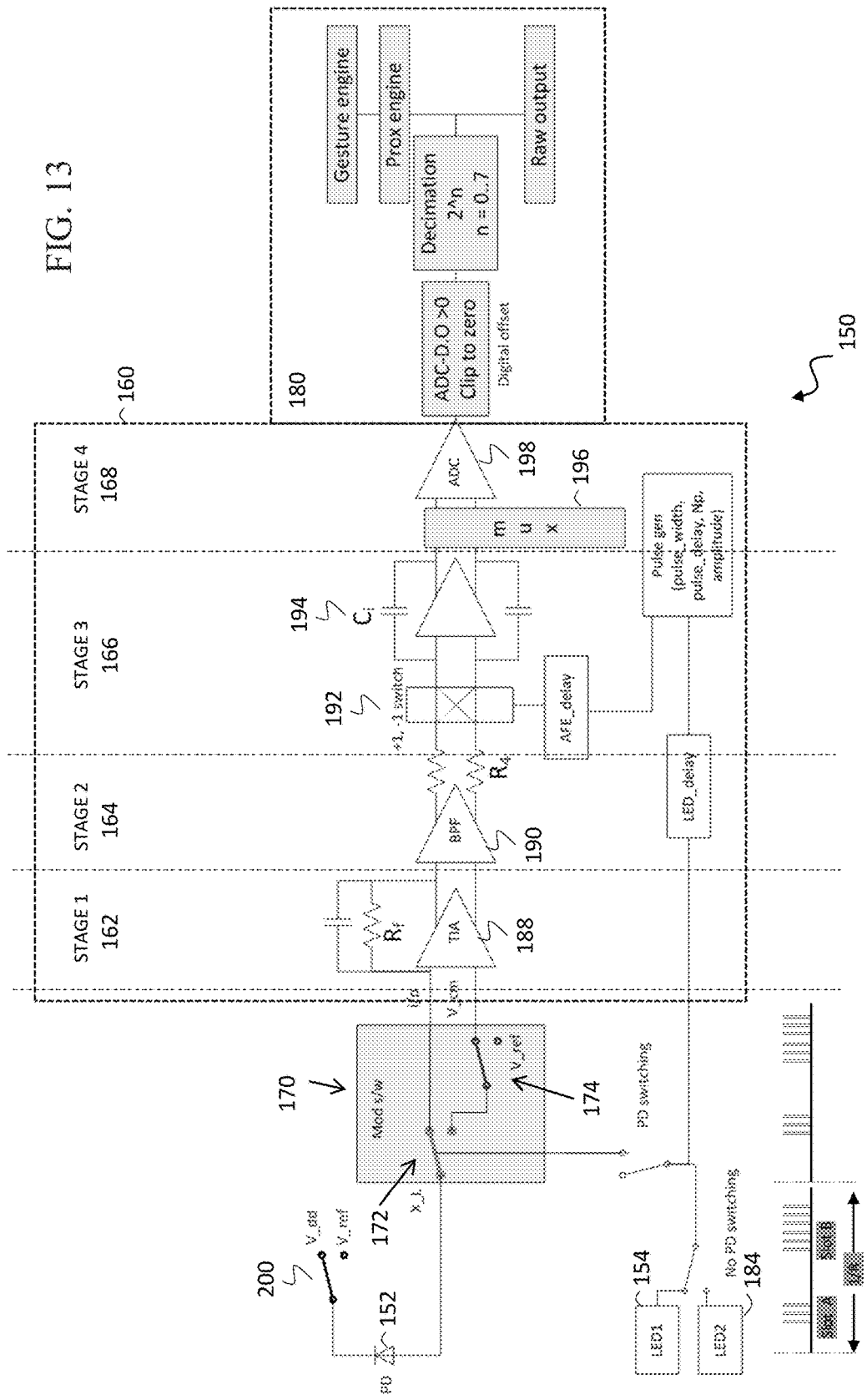
FIG. 13 is a simplified circuit diagram of a circuit architecture with mode switching, according to some embodiments of the disclosure.

Turning to FIG. 13, FIG. 13 is a simplified circuit diagram of a circuit architecture 150 with mode switching, according to some embodiments of the disclosure. Such an architecture can be used for one or more of detecting and measuring incoming signals from a target source at a sensor and detecting, measuring, and cancelling incoming ambient signals. FIG. 13 illustrates, and descriptions provided below refer to a sensor being a photodiode. However, the same as for the descriptions above, these teachings are equally applicable to detections systems employing current detection module and mode switching as described herein configured to detect currents generated by sensors, or charge generators, other than photodiodes, such as, but not limited to, pyro-electric, piezo-electric, or capacitive sensors.

According to a specific embodiment, circuit architecture 150 may comprise a sensor 152 that detects a stimuli from a target source of interest 154, e.g. a photodiode 152 that receives light from a light source 154. Circuit architecture 150 may further include current detection module 160 comprising four stages (indicated in FIG. 13 as stages 162, 164, 166, and 168) similar to the four stages 16, 18, 20, and 22 of electrical circuit 10 described above. In addition, circuit architecture 150 may comprise a mode switch 170. Photodiode 152, LED 154, mode switch 170, and current detection module 160 illustrated in FIG. 13 may be examples of, respectively, sensor 122, target source 128, mode switch 124, and current detection module 126 illustrated in FIG. 9. Therefore, all of the discussions provided for sensor 122, target source 128, mode switch 124, and current detection module 126 are applicable to corresponding elements shown in FIG. 13, which discussions, in the interests of brevity, are not repeated here.

Comparison of FIGS. 1 and 13 reveals that FIG. 13 shows the four stages of the circuit as illustrated in FIG. 1, except that sometimes elements are denoted with different symbols. For example, the TIA 188 of FIG. 1 (stage 1) is the same as the operational amplifier (op-amp) 28 in FIG. 1, the bandpass filter (BPF) 190 of FIG. 13 (stage 2) is the same as AC element 32 of FIG. 1, the +1/−1 integration switch 192 and integrator 194 of FIG. 13 (stage 3) represent the same function as SW1 and integrators 38(1) and 38(2) of FIG. 1. Similar to FIG. 1, in FIG. 13, positive and negative integrated values are provided to the ADC 198 of stage 4, e.g. via a multiplexer 196 shown in configured to select one value at a time. Similar to FIG. 1, stage 1 of FIG. 13 is used to reduce noise and stabilize the circuit, stage 2 of FIG. 13 is used to remove DC from TIA bias as well as current generated by sensor 152 (e.g. to provide first level immunity to low frequency ambient signals), stage 3 of FIG. 13 is used for integrating both the positive and the negative transient values (e.g. to provide second level immunity to ambient signals), while stage 4 of FIG. 13 is used to digitize the integrator output.

Optionally, circuit architecture could include circuitry 180 for using measurements of the circuit 160 in further digital signal processing, e.g. for gesture and/or proximity determinations. Optionally, circuit architecture may be configured to work with more than one target source, as shown with LED2 184. Further, photodiode 152 may be connected to switch 200 for management of photodiode bias, which switch may be shorted during the times the photodiode is off.

In an embodiment, logic signals sent to the LED driver to pulse the target LED 154 (or any other target source) can be simply directed to the switch 172 so that it pulses similar to the LED. This is shown as "PD switching" switch that directs LED pulse signals to the switch 172.

Mode switch 170 may be used to switch between measuring signals from the target source 154 and measuring integrated ambient charge. In one embodiment, as shown in FIG. 13, mode switch 170 may be implemented by including two switches, switches 172 and 174, connected in parallel. In various implementations, mode switch 170 may be used to e.g. measure LED light synchronized to the LED pulse generator circuits or it may be used to measure ambient light. Depending on the timing and connection of the mode switch 170, four different tasks can be carried out by the same circuit architecture, as described in further detail below.

Figure 14:
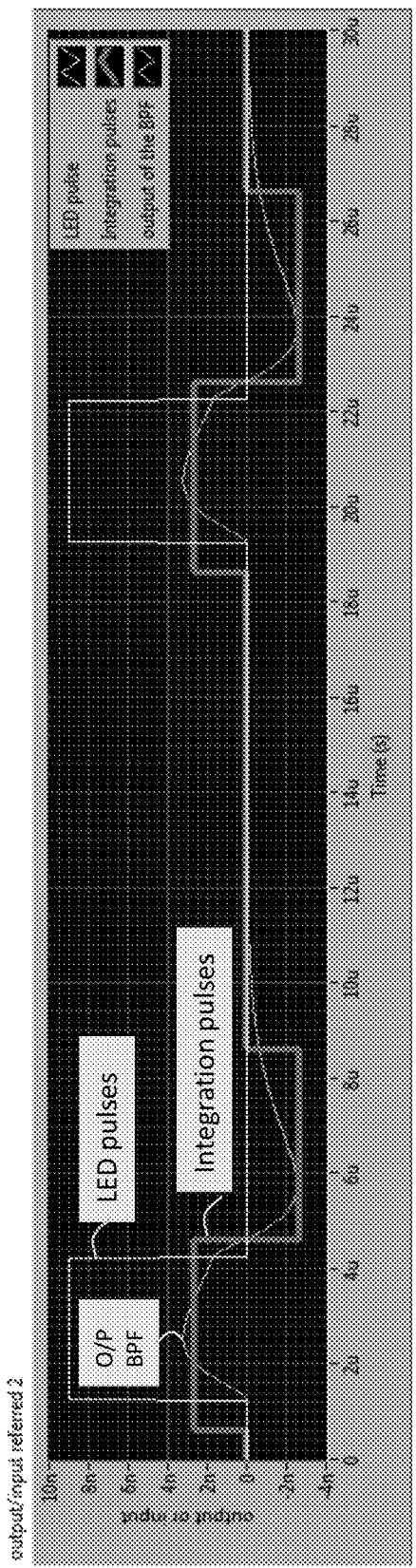
FIG. 14 is a graph showing an LED pulse input to a mode switch over time, according to some embodiments of the disclosure.

In a first mode (normal mode), mode switch 170 is used as a bypass to connect the output of sensor 152 to TIA 188 of the first stage of the current detection module 160 and is primarily used to measure the response to an LED pulse, in the same manner as described above with reference to electrical circuit 10 (therefore, all of the discussions provided above for circuit 10 are applicable here). The response of the rest of the circuit is illustrated in FIG. 14. In this mode, the goal is to measure light falling on the detector that only corresponds to the illumination by a certain target LED and reject ambient light (which could include sunlight, light from other LEDs or from any other light sources). As was described with reference to electrical circuit 10 and illustrated in FIG. 14, this is accomplished in four stages: (1) amplify the photocurrent and convert it to voltage (TIA stage), (2) pass the output of stage 1 through the BPF 190 to remove the DC portion of the photocurrent which predominantly consists of the ambient light since the LED pulse is relatively short in time duration (see LED pulses and output of BPF in FIG. 14), (3) integrate the AC output of stage 2 with the integrator 192-194 that switches sign at the zero crossing (see integration pulses in FIG. 14), and 4) digitize the integrator output using ADC 198, with an optional MUX 196 to allow multiple channels to share a single ADC.

As mentioned above, in the first mode, current detection module 160 can provide two levels of protection from ambient light. First, low DC light is reduced or blocked in stage 2. Then, positive and negative integrations by the integrator of stage 3 further reduce or block any remaining ambient light. Thus, the architecture 150 allows cancelling ambient signals without contributing additional computational load to the circuit. As used herein, in this context, the term "cancelling" refers to cancelling ambient signals, reducing ambient signals, or rendering ambient signals below the noise of the current detection module.

Thus, the mode switch 170 is used as a bypass and the rest of the circuit architecture cancels ambient light. In one example, pulsed LED light falls on the mode switch 170. FIG. 14 shows a graph of an LED pulse input to a mode switch 170 over time, according to some embodiments of the disclosure. The blinking LED light results in sensor 152 generating current pulses as shown in FIG. 14 with ""LED pulses". As shown in the circuit architecture 150, the square electrical pulses generated by sensor 152 in response to the light generated by LED 154 are input into the TIA 188, and the pulses may be band pass filtered in stage 1 (e.g. with the low-pass filter 30 as shown in FIG. 1). The pulses are then passed through an AC filter to remove the DC (i.e. through the BPF 190 of stage 2), where the output of this stage is shown in FIG. 14 with "O/P BPF." An integrator is used to recover the charge, which is represented by the area under the curve O/P BPF, and to cancel any DC that passed through the BPF 190. The integrator uses positive integration in a first (positive) phase of the cycle, and negative integration in the second (negative) phase of the cycle in order to add both parts of the cycle and capture the charge. In the first mode, the operations in the four stages of the current detection module as described herein result in an excellent rejection of the ambient light while only measuring the total number of photons reaching the detector from the LED pulse of the target LED. In order to enable such operation, various parts of the architecture 150 need to be synchronized, where, besides being provided by the design choices made in implementing various elements of the architecture 150, the synchronization may be controlled/managed by mode switch 170. Synchronization is also important for other modes of operation of the current detection module described herein. Such synchronization is described below with reference to FIGS. 15A-15D.

FIGS. 15A-15D show timing diagrams of four modes of operation of the detection system with mode switching, according to some embodiments of the disclosure. Each of FIGS. 15A-15D illustrate five rows that show the synchronization in time between various elements. The first row in each of the FIGS. 15A-15D illustrates state of the mode switch 170. The second row in each of the FIGS. 15A-15D illustrates stimuli (signal) generated by the source of interest (e.g. LED pulses generated by the target LED). The third row in each of the FIGS. 15A-15D illustrates input signal provided to the first stage (TIA 188) of the current detection module. The fourth row in each of the FIGS. 15A-15D illustrates output of the second stage (BPF 190) of the current detection module. The fifth row in each of the FIGS. 15A-15D illustrates switching of the integration sign by the switch 192 in stage 3 of the current detection module. The timing diagrams of FIGS. 15A-15D represent the relative sequence of events in the signal chain of receiving and processing signals. Synchronization between the elements of the detection system described herein refers to the fact that these events have specific and well defined relationship in each of the measurement modes.

The timing diagram for the first mode is illustrated in FIG. 15A. In the first mode, the arrival of light from the LED 154 (or a stimulus generated by any other target source) at the photodiode 152 (or any other appropriate sensor), sets off a sequence of events. In other words, arrival of signal pulses generated by the target source at the sensor controls the timing of operations performed by the current detection module. First row of FIG. 15A illustrates that, in the first mode, the mode switch 170 is closed (i.e. the output of the photodiode 152 is connected to the first stage input of the current detection module 160). LED pulses generated by the LED 154 (shown in the second row of FIG. 15A) are detected by the photodiode 152 and the photodiode 152 generates current that flows to the TIA 188 (shown in the third row of FIG. 15A). There normally is a certain time delay between the LED pulses shown in the second row and TIA pulses shown in the third row of FIG. 15A (and other FIG. 15), as a person of ordinary skill in the art would immediately recognize, but since this delay is common and does not relate to the synchronization of the elements of the detection system described herein, it is not illustrates in FIG. 15A (and other FIG. 15).

Values of the stimulus generated by the target source (e.g. width of the LED pulse) as well as various circuit elements of the current detection module, such as e.g. bandwidth of the TIA 188, corner frequencies of the BPF 190, etc., define the time delay (shown in FIG. 15A as "$t_{delay}$") from the beginning of the LED pulse to the time the zero crossing occurs in the output of the BPF 190. In other words, the location of the zero crossing depends on the value settings for the target stimulus and the values of the circuit elements of the current detection module 160. All of these values are fixed by the circuit or the user (e.g. the user provides the settings for the target stimulus) and thus the zero crossing occurs at a specific time $t_{delay}$ from the application of the stimulus. The integration sign should be changed at the time the zero crossing occurs. Since it is possible for the detection system to determine when the zero crossing occurs for a particular target source of interest, the system may be configured to set the timing of the integration switch 192 to switch from +1 to −1 integration in dependence (i.e. with respect to) the stimulus so that the transition of the switch 192 from +1 to −1 coincides with the zero crossing. This is illustrated in FIG. 15A where the integration sign shown in the fifth row changes at the same time as zero crossing in BPF output occurs. It is this specific relationship that allows the current pulse from the input to the TIA 188 to be integrated in such a way that both the positive and the negative output from the BPF filter 190 contribute to the measured signal, i.e. they are added. Any ambient light, irrespective of its frequency or shape, is quite unlikely to coincide precisely to this internally generated integration switch and thus, on an average, is cancelled during the positive and negative integration phases. When many of these pulses are added, due to such synchronization between the target source and the current detection system, current pulses resulting from the target source will continue to add to the previous values. On the other hand, at the output of the integration of stage 3, current values from the ambient sources will have values that are sometimes positive and sometimes negative (because the integration sign is not switched synchronously with the ambient sources), and thus will be averaged towards zero. Thus, the current detection module 160 allows synchronizing the sign change of the integration of stage 3 to the pulsed signal of interest, so that the integrator output is added for the pulsed signal of interest but the ambient signals are, on average, cancelled out due to lack of their synchronization with the sign change.

It should be noted that the timing diagram for the first mode illustrated in FIG. 15A is comparable to the timing diagram illustrated in FIG. 3, except that FIG. 3 illustrates various metrics in the same graph (as opposed to rows of FIG. 15A) and illustrates an input current generated by the sensor ("input photocurrent pulse") instead of a pulse generated by the target source ("LED pulse").

In a second mode (which could be referred to as a "floating" sensor mode), one goal is to measure the ambient contributions only. In such a case, there is no natural pulsing of ambient sources, as was the case with the pulsed target source 154, (because, unlike target sources that may be controlled, ambient sources are typically not controlled). However, in this mode, the mode switch 170 may be operated in such a way that the sensor 152 itself can be used as the integrator, artificially generating what looks, to the current detection module 160, as a current pulse similar to that generated in the first mode when LED pulse is detected. To that end, capacitance associated with the sensor 152 (e.g. the designated capacitive elements as well as parasitic capacitive elements as shown in FIG. 10) can be used to integrate the charge generated by the sensor as a result of receiving stimuli from ambient sources.

The cycle of the second mode may begin by the mode switch 170 ensuring that the output of sensor 122 is not connected to anything (this may be achieved e.g. by having mode switch in position 144 illustrated in FIG. 12 and may be considered as the mode switch 170 being open). This is shown in the first row of FIG. 15B providing the timing diagram for the second mode.

At the time the mode switch 170 is open, signals generated by one or more ambient sources are detected by the sensor 152, resulting in the sensor 152 generating charge on the capacitors of the sensor. Target sources 154 may be off (i.e. not generating signals that are detected by the sensor 152), as shown in the second row of FIG. 15B (no LED pulse). Because the output of the sensor 152 is not connected to anything, current cannot flow, so the charge accumulates/integrates on the capacitive elements of the sensor 152. This continues for a certain time period (which could be referred to as "integration time" or "floating time"), which could e.g. be user-defined or could be dynamically determined by the detection system based on the maximum charge that can be stored.

Figure 15B:
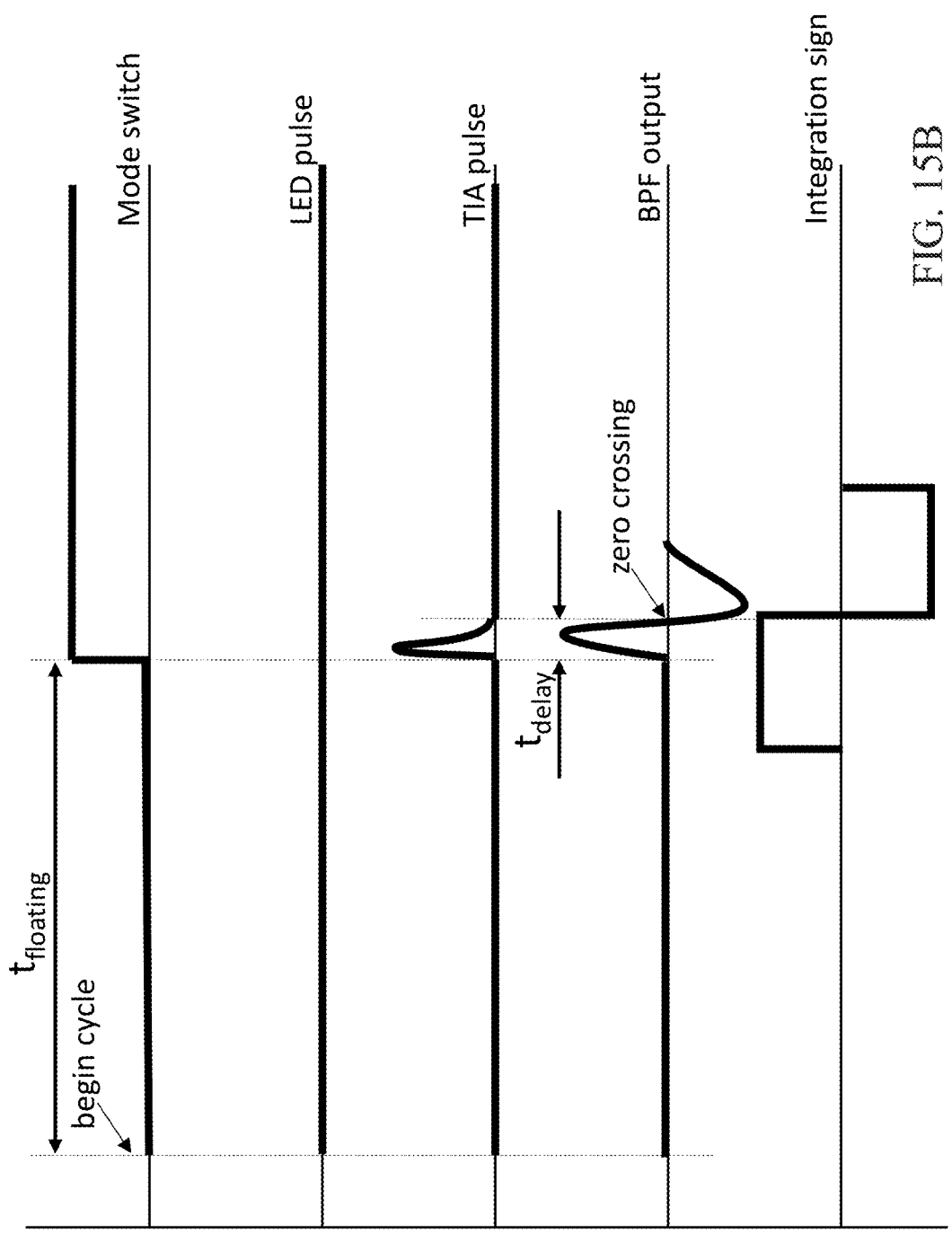

After this certain time period, the mode switch 170 connects the output of sensor 152 to the current detection module 160, as shown in the first row of FIG. 15B with the mode switch being "closed." As a result of making this connection, the charge stored on the capacitive elements of the sensor 152 will discharge through the current detection module (e.g. through the TIA 188) and make a pulse of current, shown in the third row of FIG. 15B. As far as the rest of the current detection module 160 is concerned, this pulse of current looks just like a pulse received from the sensor 152 in the first mode as a result of sensor 152 detecting a pulse generated by the target source. In other words, operation when, in the second mode, the mode switch 170 first makes sure that the output of sensor 152 is not connected to anything and accumulates charge and then connects the output of sensor 152 to the current detection module 160, artificially generates a current pulse that is provided to the TIA 188. The rest of the architecture of the current detection module 160 may then be used in a manner analogous to how a current pulse was processed in the first mode because, as described above for the first mode, it is the receipt of this current pulse by the current detection module that defines the timing of other operations and elements of the current detection module. For example, as described above, occurrence of zero-crossing (shown in the fourth row of FIG. 15B) happens after a predefined time period after the receipt of the TIA pulse, and the current detection module 160 is configured to switch the integrator sign of stage 3 at the time when the zero-crossing takes place (shown in the fifth row of FIG. 15B).

Thus, in the second mode of operation of the current detection module 160, providing an artificially generated current pulse to the current detection module 160 (by means of the mode switch 170) allows benefiting from the synchronization between the elements provided by the module to accurately measure the pulse. In this mode, because the pulse is generated as a result of the sensor 152 detecting contributions from the ambient sources only (target sources were off), the value generated by the current detection module is representative of contributions to the sensor-generated current signal due to the ambient sources. In other words, a current pulse artificially generated in the second mode, when integrated, directly represents the total accumulated charge and hence the strength of the ambient.

In some embodiments of the second mode, stage 2 (i.e. BPF 190) of the current detection module 160 may be removed/bypassed because in this mode it is not necessary to eliminate low frequency/DC contributions typical of ambient light in the first mode. Thus, the current pulse shaped by the TIA 188 may be integrated directly, without passing through the BPF stage. In such embodiments, the timing of the integration switch may be adjusted to include the entire integration of the pulse in the positive or the negative cycle. When the second stage is bypasses, zero-crossing point is defined in the output of the TIA 188.

The switching integrator stage (stage 3) is maintained in the second mode. The positive-negative cycle removes many integrator offsets. If the integration time on the sensor (i.e. the time the sensor 152 is floating) is $\tau$ and contributions from the ambient sources result in sensor 152 generating current $i_{amb}$, the total charge $Q=i_{amb}\tau$ can be measured by the detection system as described herein with high SNR by simply increasing the floating time until the charge accumulated on the sensor 152 is greater than the measurement noise floor.

In some implementations, internal leakage currents may limit the floating time. For example, for a relatively large photodiode of 100 µm in size, one lux of light will make for roughly 4-5 pA of current, which, when integrated for 1 ms, results in 8 fC of accumulated charge that can be measured.

As the foregoing illustrates, the same current detection module can be used to either measure contributions from the ambient sources or contributions from synchronous pulse(s) generated by a target source.

In an embodiment, mode switching functionality used to create a pulse in the ambient input as described for the second mode may be implemented with the mode switch 170 comprising the switches 172 and 174. In such an embodiment, the first switch 172 may be connected to the second switch 174. When the second switch 174 is open, the charge from the sensor 152 has nowhere to go and the mode switch 170 integrates the accumulated charge on the sensor. Then the second switch 174 is closed to the TIA 188, and the charge is transmitted through to the TIA 188 like a pulse of target source in the first mode. In this manner, ambient signals are captured and turned into pulsed signals. The pulses are then processed by the rest of the circuit in the same manner as the target source pulses were processed in the first mode.

A third operating mode may also be used to measure ambient contributions only, but this mode may be used particularly advantageously in a presence of fairly strong contributions from ambient sources (e.g. in presence of strong ambient light). In such situations, it may be undesirable to integrate the charge on the sensor 152 as was done in the second mode because, when ambient contributions are strong, such integration is likely to lead to saturation of the sensor 152 (i.e. reaching the maximum amount of charge that the capacitive elements of the sensor 152 are able to hold) in a very short amount of time. A saturated sensor cannot produce accurate measurements because it is clipped at the maximum values. This mode of operation may also be advantageously used with certain types of sensors that may function better when the voltage remains constant during the measurement, e.g. pyro sensors biased at a constant voltage and photodiodes for measuring intense light. In all these situations, it may be desirable to measure the current generated by the sensor 152 directly, without integrating the charge on the sensor as was done in the second mode. In such situations, the mode switch 170 can be used, again, to effectively generate what looks like a current pulse that can be processed by the current detection module 160. Thus, similar to the second mode, in the third mode, there is no natural pulsing of ambient sources but the mode switch 170 may be operated to artificially generate what looks, to the current detection module 160, as a current pulse similar to that generated in the first mode when LED pulse is detected. The rest of the architecture of the current detection module 160 may then be used in a manner analogous to how a current pulse was processed in the first mode because it is the receipt of this current pulse by the current detection module that defines the timing of other operations and elements of the current detection module (i.e., as in the second mode, it is possible to benefit from the synchronization between the elements provided by the module to accurately measure the pulse).

Figure 15C:
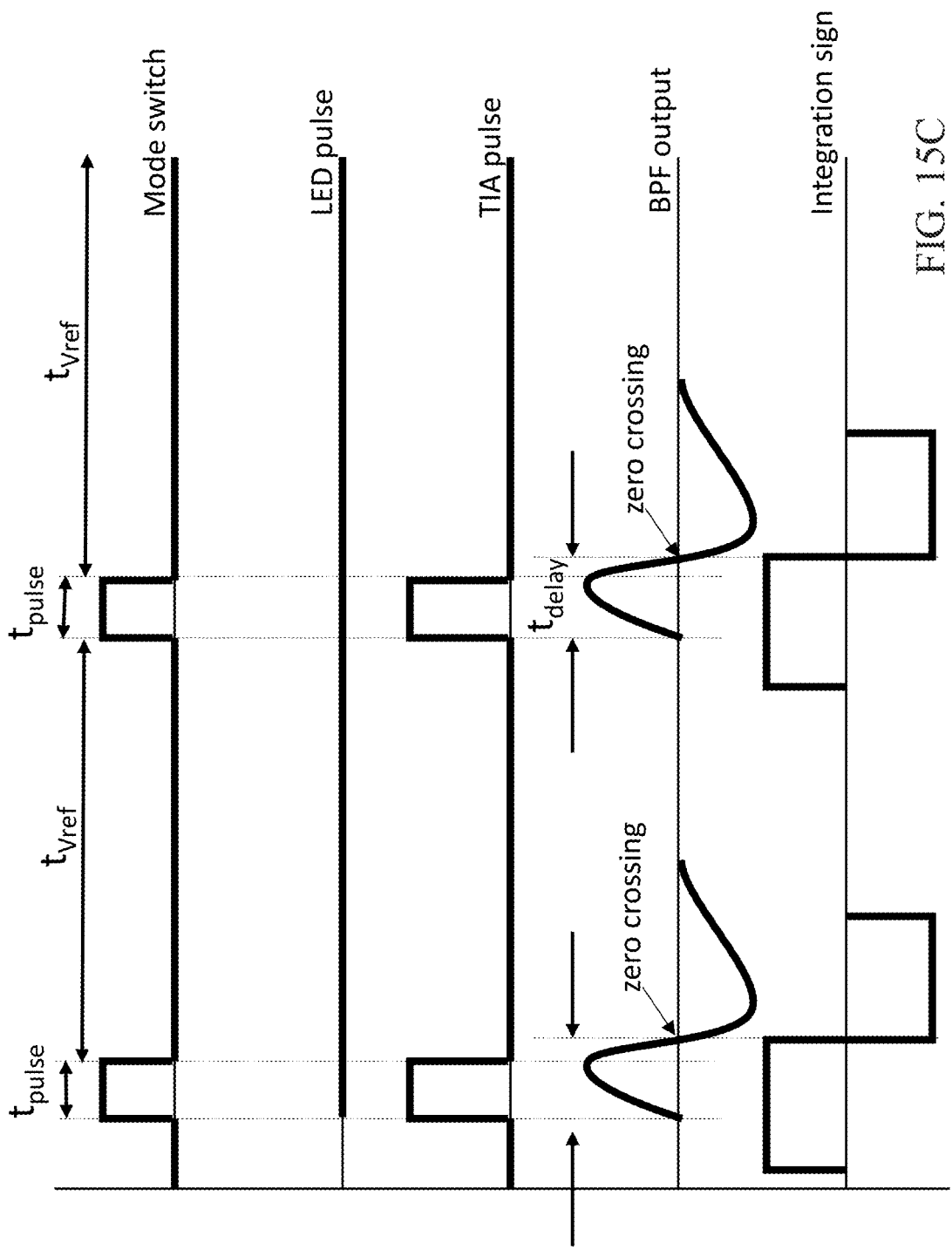

In the third mode, at certain times (shown in FIG. 15C as "$t_{V_{ref}}$") the mode switch 170 connects the output of the sensor 152 to a certain reference voltage (e.g. common mode voltage of the TIA 188, V_cm) node so that no current passes through the TIA 188 (i.e. as far as the TIA 188 is concerned, the mode switch 170 is open, as illustrated in the first row of FIG. 15C). At this time, target sources 154 may be off (i.e. not generating signals that are detected by the sensor 152), as shown in the second row of FIG. 15C (no LED pulse), and only signals generated by one or more ambient sources are detected by the sensor 152. Because the sensor 152 is connected to the reference voltage and not connected to the current detection module 160, there is no current going to the TIA 188 during the times $t_{vref}$ (as shown in FIG. 15C in the third row).

At certain other times (shown in FIG. 15C as "$t_{pulse}$"), the mode switch 170 connects the output of the sensor 152 to the input of the amplifier 188. When this happens, current (representative of the ambient source contributions) can flow from the sensor 152 to the TIA 188, resulting in the TIA 188 receiving a current pulse similar to the current pulse made, in the first mode, by the target source. The magnitude of the current pulse can be measured in the same way as described above.

Thus, in the third mode, the mode switch 170 is configured to effectively generate what looks like a current pulse from a constant stimulus arriving at the sensor 152. This is done by pulsing the mode switch 170 to connect for a specific amount of time to the amplifier's input ($t_{pulse}$) and otherwise the sensor 152 remains connected to a fixed reference voltage, e.g. to the common mode voltage of the amplifier through the switch 174 shown in FIG. 13). With such implementation, the sensor always has the same potential on its terminals and the TIA 188 does not receive current generated by the sensor 152 except for the times when that current is momentarily directed into the TIA 188, resulting in one or more current pulses on the TIA 188 as shown in the third row of FIG. 15C. Such current pulses is similar to the current pulse of from the target source of the first mode and the rest of the operation of the current detection module 160 proceeds as described above for the first and second modes, which descriptions, in the interests of brevity, are not repeated here. Fourth and fifth rows of FIG. 15C illustrate synchronization as described above.

In one embodiment, the third mode described herein could be modified by measuring sensor node between two different reference voltages, thereby measuring the changes to the sensor itself as the voltage is pulsed. This embodiment may be implemented in the same manner as the third mode described above, except that, at times shown in FIG. 15C as $t_{V_{ref}}$, the mode switch 170 connects the output of the sensor 152 to a certain reference voltage that is different from the common mode voltage V_cm. For example, if switch 174 were connected to V_ref and the switch 172 were pulsed, and if V_ref were to be different than V_cm, then the potential on the sensor is changed as switch 172 is pulsed. Thus the current flowing into the amplifier depends not only on the ambient current but also on the differences in the charge due to different potentials—V_cm when connected to the input of the amp and V_ref otherwise. This will provide input pulse to the amplifier even in the absence of any ambient. This flow of current originates purely from the changes in potential is directly proportional to the capacitance of the network. Simply, the net charge flowing into the amplifier during "pulse" is $\Delta Q = C \Delta V$ where the difference between the two potentials is $\Delta V$. As previously described herein, this capacitance (be it capacitance itself, or state of the sensor such as pyro, PZT, inductive etc.) can be changed by the environment and measured. Thus this modification of the third mode allows direct measurement of the "state of the sensor" and hence it's environment.

Figure 15D:
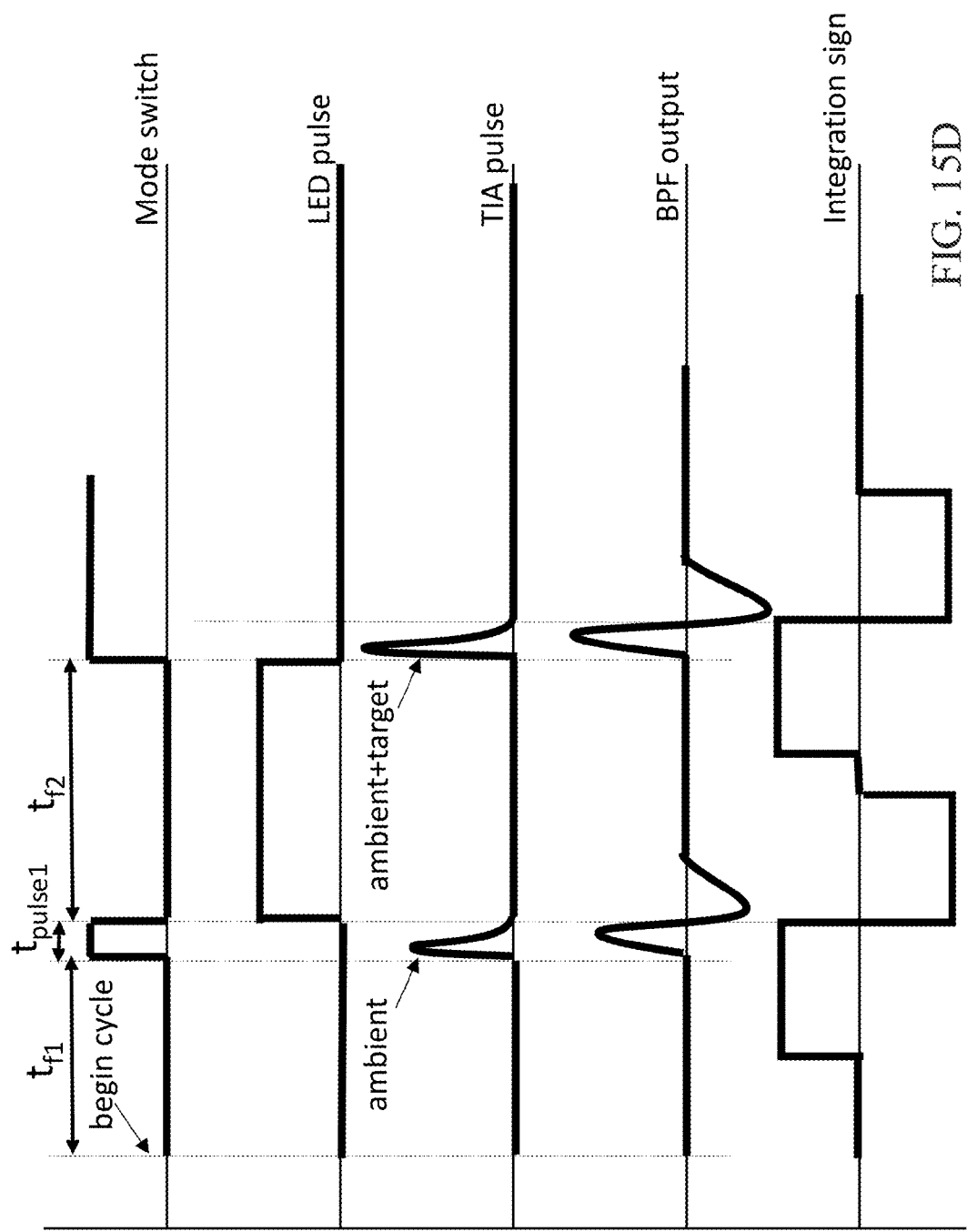

A fourth operating mode, illustrated in the timing diagram of FIG. 15D, may be considered as a combination of the first and second modes described above in that both pulsing of the target source 154 and floating of the sensor 152 are used. In this case, the sensor 152 is floating for a certain time period (shown in FIG. 15D as "$t_{f1}$") when the target source is off (in the second row of FIG. 15D, LED pulse is shown to be off during time $t_{f1}$), followed by the output of the sensor 152 being connected to the input of the TIA 188 for a certain time period (shown in FIG. 15D as "$t_{pulse1}$"), resulting in a current pulse as described above for the second mode (shown in the third row of FIG. 15D as current pulse "ambient"). Because the target source 154 was off in the time when the sensor was floating, this current pulse, when integrated (see first integration in the fifth row of FIG. 15D), directly represents the total accumulated charge and hence the strength of only the ambient.

After that, the sensor 152 is floating again for a certain time period (shown in FIG. 15D as "$t_{f2}$", which time period may but does not have to be equal to $t_{f1}$), except that now the target source is on (in the second row of FIG. 15D, LED pulse is shown to be on during time $t_{f1}$). Since the sensor 152 is floating (i.e. no current is flowing to the TIA 188) when the target source is on, during this time $t_{f2}$, the charge accumulated on the capacitive elements of the sensor 152 is due to both contributions of the ambient and the target source. Again, as in the second mode above, the output of the sensor 152 is then connected to the input of the TIA 188 for a certain time period (shown in FIG. 15D as "$t_{pulse2}$"), resulting in a current pulse as described above for the second mode (shown in the third row of FIG. 15D as current pulse "ambient+target"), except that now, because the target source 154 was on in the time when the sensor was floating, this current pulse, when integrated (see the second integration in the fifth row of FIG. 15D), directly represents the combined strength of ambient and target sources. By subtracting the value generated by the current detection module 160 indicative of measurements of the first pulse (ambient) from the value indicative of measurements of the second pulse (ambient+target), a value indicative of the contribution of the target source only is obtained.

In some embodiments of the fourth mode, the mode switch 170 may be disconnect the output of the sensor 152 from the TIA 188 immediately following the discharge of the sensor 152 in the first current pulse, as shown in FIG. 15D. However, in other embodiments, this may be done some time later, as long as the timing is such that the target source is turned on when that disconnection occurs (i.e. when the sensor 152 starts floating again).

Considerations provided above for the second mode are applicable, except for the differences in that target source is sometimes on, to the fourth mode, and, therefore, are not repeated here. In particular, in the fourth mode (as well as in the third mode), in some embodiments, the second stage (BPF) of the current detection module 160 may be bypassed and the output of the TIA 188 may be presented directly to the integrator stage.

The fourth mode may be particularly advantageous for situations where ambient light is weak or has low modulation frequency compared to pulse width, in which cases the fourth mode can provide enhanced SNR when compared to multiple pulses in the first mode.

The four modes described above are summarized in the table in FIG. 16 for the example of sensor 152 being a photodiode.

For the example of sensor 152 being a photodiode, according to various implementations, the LED light can be any color. For example, a red or a green LED light may be used. Similarly, the LED pulse width can be any selected width, and in one example, the LED pulse width is about 3 µs. In other examples, the LED pulse width is less than about 3 µs, or more than about 3 µs. Pulse width of few ns to 100's of microsecond is a typical range for LED pulsewidths. The measurements can be repeated first as a burst of pulses, which are themselves repeated at various rates ranging from 0.01 Hz to many kHz.

In other embodiments when sensor 152 is a photodiode, the target light source could be any controllable light source, not necessarily a LED. Thus, target light sources could be, but are not limited to, e.g. laser diodes, high/low pressure gas discharge sources, inorganic/organic light emitting diodes, incandescent sources, halogen sources, etc.

Variations and Implementations

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

In one example embodiment, parts or entire electrical circuits of the FIGURES may be implemented on a motherboard of an associated electronic device. The motherboard can be a general circuit board that can hold various components of the internal electronic system of the electronic device and, further, provide connectors for other peripherals. More specifically, the motherboard can provide the electrical connections by which the other components of the system can communicate electrically. Any suitable processors (inclusive of digital signal processors, microprocessors, supporting chipsets, etc.), memory elements, etc. can be suitably coupled to the motherboard based on particular configuration needs, processing demands, computer designs, etc. Other components such as external storage, additional sensors, controllers for audio/video display, and peripheral devices may be attached to the motherboard as plug-in cards, via cables, or integrated into the motherboard itself.

In another example embodiment, parts or entire electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the amplification functionalities may be implemented in one or more silicon cores in Application Specific Integrated Circuits (ASICs), Field Programmable Gate Arrays (FPGAs), and other semiconductor chips.

It is also imperative to note that all of the specifications, dimensions, and relationships outlined herein (e.g., the number of processors and memory elements, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that parts or entire electrical circuits of the FIGURES and its teachings are readily scalable and can accommodate a large number of components, as well as more complicated/sophisticated arrangements and configurations. Accordingly, the examples provided should not limit the scope or inhibit the broad teachings of parts or entire electrical circuits as potentially applied to a myriad of other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Although the claims are presented in single dependency format in the style used before the USPTO, it should be understood that any claim can depend on and be combined with any preceding claim of the same type unless that is clearly technically infeasible.

What is claimed is:

1. A detection system comprising:
   a sensor configured to generate a current signal, the current signal comprising at least a first portion comprising a contribution from a target source and/or a second portion comprising a contribution from one or more sources other than the target source;
   a current detection module configured to receive the current signal generated by the sensor and generate a digital value indicative of the first portion of the current signal and/or a digital value indicative of the second portion of the current signal; and
   a mode switch configured to set the current detection module to operate in one of a first mode, a second mode, and a third mode, wherein:
      in the first mode, the current detection module is configured to generate the digital value indicative of the first portion,
      in the second mode, the current detection module is configured to generate the digital value indicative of at least the second portion when the contribution from the one or more sources other than the target source is in a first range of values, and
      in the third mode, the current detection module is configured to generate the digital value indicative of at least the second portion when the contribution from the one or more sources other than the target source is in a second range of values, the second range of values having an upper end higher than an upper end of the first range of values.

2. The detection system according to claim 1, wherein the mode switch and the target source are synchronized so that the mode switch is configured to set the current detection module to operate in the first mode when the target source is generating the contribution to the current signal, and configured to set the current detection module to operate in the second mode or in the third mode when the target source is not generating the contribution to the current signal.

3. The detection system according to claim 1, wherein the mode switch is further configured to set the current detection module to operate in a fourth mode,
   wherein in the fourth mode,
      the mode switch is configured to:
         set the current detection module to operate in the second mode for a first period of time while the target source is not generating the contribution to the current signal to generate a first digital value indicative of the second portion in absence of the first portion, and
         set the current detection module to operate in the second mode for a second period of time while the target source is generating the contribution to the current signal to generate a second digital value indicative of a total of the first portion and the second portion, and
      the current detection module is configured to generate the digital value indicative of the first portion by subtracting the first digital value from the second digital value.

4. The detection system according to claim 1, wherein, in the second mode, the mode switch is configured to enable charge accumulation on one or more capacitive elements of the sensor for a duration of a first time interval followed by discharge of the one or more capacitive elements of the sensor to the current detection module for a duration of a second time interval thereby providing a pulsed current signal to the current detection module.

5. The detection system according to claim 4, wherein the one or more capacitive elements of the sensor accumulate charge for a duration of a first time interval followed by discharge of the one or more capacitive elements of the sensor to the current detection module for a duration of a second time interval thereby providing a pulsed current signal to the current detection module.

6. The detection system according to claim 1, wherein, in the third mode, the mode switch is configured to maintain charge on a capacitor of the sensor at a reference value for a duration of a first time interval followed by a second time interval during which the mode switch is configured to release maintaining of the charge on a capacitor at the reference value while enabling the capacitor of the sensor to discharge to the current detection module thereby providing a pulsed current signal to the current detection module.

7. The detection system according to claim 1, wherein the sensor comprises one of a photosensor, a capacitance sensor, an impedance sensor, a magnetic field sensor, or a piezo-electric film.

8. The detection system according to claim 1, wherein the contribution to the current signal from the target source comprises a pulse or a series of repeating pulses synchronized to the current detection module.

9. The detection system according to claim 1, wherein the current detection module comprises:
   a first stage comprising a trans-impedance amplifier configured to amplify the current signal and generate a low noise signal;
   a second stage comprising a high pass filter configured to convert the low noise signal into an alternating current (AC) signal having a positive amplitude, a negative amplitude, and a zero cross-over point between the positive amplitude and the negative amplitude;
   a third stage comprising:
      a positive integrating amplifier configured to receive the positive amplitude of the AC signal and generate a positive integrated value over an integration period; and
      a negative integrating amplifier configured to receive the negative amplitude of the AC signal and generate a negative integrated value over the integration period; and
   a fourth stage comprising at least an analog-to-digital converter (ADC) configured to receive the positive and negative integrated values and generate the digital value indicative of the first portion of the current signal and/or the digital value indicative of the second portion of the current signal based on the positive and negative integrated values.

10. The detection system according to claim 9, wherein the trans-impedance amplifier includes an operational amplifier with a feedback loop comprising a feedback capacitor and a feedback resistor and a low pass filter.

11. The detection system according to claim 9, wherein the second stage includes an AC source and a capacitor that provides AC coupling.

12. The detection system according to claim 9, wherein the third stage includes a switch configured to change from the positive integrating amplifier to the negative integrating amplifier at the occurrence of the zero cross-over point.

13. The detection system according to claim 12, wherein the switching action of the switch is configured by a timer.

14. The detection system according to claim 13, wherein the timer is configured to provide a clock synchronized with a frequency of the target source.

15. The detection system according to claim 9, wherein the second stage is bypassed in the second mode and/or the third mode.

16. The detection system according to claim 9, wherein the target source is a synchronous light source.

17. The detection system according to claim 16, wherein a pulse of the synchronized light source has a duration of $\tau$, a bandwidth of the second stage is approximately $1/\tau$, and a corner frequency of the high pass filter is set as $0.5/\tau$.

18. A detection system comprising:
first means for generating a current signal, the current signal comprising at least a first portion comprising a contribution from a target source and/or a second portion comprising a contribution from one or more sources other than the target source, and generating a digital value indicative of the first portion of the current signal and/or a digital value indicative of the second portion of the current signal; and
second means for setting the first means to operate in one of a first mode, a second mode, and a third mode, wherein:
in the first mode, the first means is configured to generate the digital value indicative of the first portion,
in the second mode, the first means is configured to generate the digital value indicative of at least the second portion when the contribution from the one or more sources other than the target source is in a first range of values, and
in the third mode, the first means is configured to generate the digital value indicative of at least the second portion when the contribution from the one or more sources other than the target source is in a second range of values, the second range of values having an upper end higher than an upper end of the first range of values.

19. The detection system according to claim 18, wherein the second means and the target source are synchronized so that the second means is configured to set the first means module to operate in the first mode when the target source is generating the contribution to the current signal, and configured to set the first means to operate in the second mode or in the third mode when the target source is not generating the contribution to the current signal.

20. A detection system comprising:
a sensor configured to generate a current signal indicative of the sensor detecting a stimuli that comprises a pulse or a series of repeating pulses generated by a target source;
a current detection module having a predetermined phase relationship between operation of the current detection module and the pulse or the series of repeating pulses generated by the target source, and configured to determine a contribution to the current signal due to the detected stimuli from the target source.

21. The detection system according to claim 20, wherein the current detection module comprises:
a first stage comprising a trans-impedance amplifier configured to amplify the current signal and generate a low noise signal;
a second stage comprising a high pass filter configured to convert the low noise signal into an alternating current (AC) signal having a positive amplitude, a negative amplitude, and a zero cross-over point between the positive amplitude and the negative amplitude;
a third stage comprising:
a positive integrating amplifier configured to receive the positive amplitude of the AC signal and generate a positive integrated value over an integration period; and
a negative integrating amplifier configured to receive the negative amplitude of the AC signal and generate a negative integrated value over the integration period; and
a fourth stage comprising at least an analog-to-digital converter (ADC) configured to receive the positive and negative integrated values and determine the contribution to the current signal due to the detected stimuli based on the positive and negative integrated values.

22. The detection system according to claim 20, wherein the current signal further comprises a contribution due to the sensor detecting a stimuli from one or more sources other than the target source, and the detection system further comprises a mode switch configured to control the current detection module to operate in a first mode or a second mode, wherein
the current detection module is configured to determine the contribution to the current signal due to the detected stimuli from the target source when the current detection module operates in the first mode, and
the current detection module is configured to determine the contribution to the current signal due to the detected stimuli from one or more sources other than the target source when the current detection module operates in the second mode.

23. The detection system according to claim 22, wherein the mode switch is configured to control the current detection module to operate in one of the first mode, the second mode, or a third mode, and wherein
the current detection module is configured to operate in the second mode when the contribution from the one or more sources other than the target source is in a first range of values, and
the current detection module is configured to operate in the third mode when the contribution from the one or more sources other than the target source is in a second range of values, the second range of values having an upper end higher than an upper end of the first range of values, to determine the contribution to the current signal due to the detected stimuli from one or more sources other than the target source.

24. The detection system according to claim 22, wherein the mode switch is configured to control the current detection module to operate in one of the first mode, the second mode, or a third mode, and wherein, in the third mode, the current detection module is configured to:
operate in the second mode for a first period of time during which the sensor is not detecting the stimuli from the target source to determine the contribution to the current signal due to the detected stimuli from one or more sources other than the target source in absence of the contribution to the current signal due to the detected stimuli from the target source,
operate in the second mode for a second period of time during which the sensor is detecting the stimuli from the target source to determine a combined contribution due to the sensor detecting both the stimuli from the target source and the stimuli from one or more sources other than the target source, and determine the contribution to the current signal due to the stimuli from the target source by subtracting the contribution determined for the first period of time from the combined contribution determined for the second period of time.

25. The detection system according to claim 20, wherein:

the current signal is a first current signal, further comprising a contribution due to the sensor detecting a stimuli from one or more sources other than the target source, the sensor is configured to generate the first current signal for a first time period during which the sensor is detecting both the stimuli from the target source and the stimuli from one or more sources other than the target source, the sensor is further configured to generate a second current signal for a second time period during which the sensor is detecting the stimuli from one or more sources other than the target source and not detecting the stimuli from the target source, the current detection module is configured to determine the contribution to the current signal due to the stimuli from the target source based on a difference between the first current signal and the second current signal.

26. The detection system according to claim 20, wherein:

the pulse generated by the target source or each pulse of the series of repeating pulses generated by the target source has a duration of $\tau$, the current detection module comprises a trans-impedance amplifier configured to amplify the current signal and generate a low noise signal and a high pass filter configured to convert the low noise signal into an alternating current (AC) signal having a positive amplitude, a negative amplitude, and a zero cross-over point between the positive amplitude and the negative amplitude, and the predetermined phase relationship between operation of the current detection module and the pulse or the series of repeating pulses generated by the target source comprises the bandwidth of the high pass filter being $1/\tau$, and a corner frequency of the high pass filter being $0.5/\tau$.

27. The detection system according to claim 23, wherein:

the current detection module comprises a clock, and the current detection module having the predetermined phase relationship with the pulse or the series of repeating pulses generated by the target source comprises one or more frequencies present in the pulse or the series of repeating pulses generated by the target being synchronized to the clock.

* * * * *